(12) United States Patent
Gammie et al.

(10) Patent No.: US 10,285,686 B2
(45) Date of Patent: May 14, 2019

(54) TRANSAPICAL MITRAL VALVE REPAIR METHOD

(71) Applicant: UNIVERSITY OF MARYLAND, BALTIMORE, Baltimore, MD (US)

(72) Inventors: James Gammie, Stevenson, MD (US); Rahul Patel, Baltimore, MD (US); Mehrdad Ghoreishi, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 136 days.

(21) Appl. No.: 14/478,325

(22) Filed: Sep. 5, 2014

(65) Prior Publication Data
US 2015/0032127 A1    Jan. 29, 2015

Related U.S. Application Data

(60) Division of application No. 14/138,857, filed on Dec. 23, 2013, now Pat. No. 8,852,213, which is a
(Continued)

(51) Int. Cl.
*A61B 17/04* (2006.01)
*A61F 2/24* (2006.01)
(Continued)

(52) U.S. Cl.
CPC ...... *A61B 17/0469* (2013.01); *A61B 17/0401* (2013.01); *A61B 17/0485* (2013.01);
(Continued)

(58) Field of Classification Search
CPC .. A61F 2/2457; A61F 2/2466; A61B 17/0469; A61B 17/062; A61B 17/04;
(Continued)

(56) References Cited

U.S. PATENT DOCUMENTS 3,131,957 A    5/1964   Musto
3,752,516 A    8/1973   Mumma
(Continued)

FOREIGN PATENT DOCUMENTS

EP         0791330         6/2005
WO    WO 2006/078694      7/2006
(Continued)

OTHER PUBLICATIONS

Office Action for U.S. Appl. No. 11/683,282, dated Feb. 27, 2009, 6 pages.
(Continued)

*Primary Examiner* — Christopher L Templeton
(74) *Attorney, Agent, or Firm* — Pui Tong Ho

(57) ABSTRACT

Methods and devices for repairing a cardiac valve. A minimally invasive procedure includes creating an access in the apex region of the heart through which one or more instruments may be inserted. The device can implant artificial heart valve chordae tendineae into cardiac valve leaflet tissues to restore proper leaflet function and prevent reperfusion. The device punctures the apex of the heart and travels through the ventricle. The tip of the device rests on the defective valve and punctures the valve leaflet. A suture or a suture/guide wire combination is inserted, securing the top of the leaflet to the apex of the heart. A resilient element or shock absorber mechanism adjacent to the outside of the apex of the heart minimizes the linear travel of the device in response to the beating of the heart or opening/closing of the valve.

2 Claims, 20 Drawing Sheets

Related U.S. Application Data continuation of application No. PCT/US2012/043761, filed on Jun. 22, 2012.

(60) Provisional application No. 61/550,772, filed on Oct. 24, 2011, provisional application No. 61/501,404, filed on Jun. 27, 2011.

(51) Int. Cl.
*A61B 17/00* (2006.01)
*A61B 17/06* (2006.01)
*A61B 17/062* (2006.01)

(52) U.S. Cl.
CPC ...... *A61B 17/062* (2013.01); *A61B 17/06066* (2013.01); *A61B 17/06166* (2013.01); *A61F 2/2457* (2013.01); *A61B 2017/00243* (2013.01); *A61B 2017/00783* (2013.01); *A61B 2017/0404* (2013.01); *A61B 2017/0406* (2013.01); *A61B 2017/047* (2013.01); *A61B 2017/0409* (2013.01); *A61B 2017/0417* (2013.01); *A61B 2017/0464* (2013.01); *A61B 2017/06171* (2013.01); *A61F 2/2466* (2013.01)

(58) Field of Classification Search
CPC ............ A61B 17/0482; A61B 17/0483; A61B 2017/00243; A61B 2017/00783; A61B 2017/0409; A61B 2017/0417; A61B 2017/0464
USPC .............. 606/139, 148, 144, 232; 623/13.11, 623/13.14
See application file for complete search history.

(56) References Cited

U.S. PATENT DOCUMENTS

| | | |
|---|---|---|
| 4,403,797 A | 9/1983 | Ragland, Jr. |
| 5,144,961 A | 9/1992 | Chen et al. |
| 5,147,316 A | 9/1992 | Castillenti |
| 5,312,423 A | 5/1994 | Rosenbluth et al. |
| 5,391,176 A | 2/1995 | de la Torre |
| 5,405,352 A | 4/1995 | Weston |
| 5,454,821 A | 10/1995 | Harm et al. |
| 5,472,446 A | 12/1995 | de la Torre |
| 5,507,754 A | 4/1996 | Green et al. |
| 5,527,323 A | 6/1996 | Jervis et al. |
| 5,554,184 A | 9/1996 | Machiraju |
| 5,626,614 A * | 5/1997 | Hart .............................. 606/232 |
| 5,643,293 A | 7/1997 | Kogasaka et al. |
| 5,681,331 A | 10/1997 | de la Torre et al. |
| 5,716,368 A | 2/1998 | de la Torre et al. |
| 5,727,569 A | 3/1998 | Benetti et al. |
| 5,728,109 A | 3/1998 | Schulze et al. |
| 5,746,752 A | 5/1998 | Burkhart |
| 5,769,862 A | 6/1998 | Kammerer et al. |
| 5,797,928 A | 8/1998 | Kogasaka |
| 5,824,065 A | 10/1998 | Gross |
| 5,931,868 A | 8/1999 | Gross |
| 5,957,936 A | 9/1999 | Yoon et al. |
| 5,971,447 A | 10/1999 | Steck, III |
| 6,010,531 A | 1/2000 | Donlon et al. |
| 6,074,417 A | 6/2000 | Peredo |
| 6,269,819 B1 | 8/2001 | Oz et al. |
| 6,332,893 B1 | 12/2001 | Mortier et al. |
| 6,562,051 B1 | 5/2003 | Bolduc et al. |
| 6,626,930 B1 | 9/2003 | Allen et al. |
| 6,629,534 B1 | 10/2003 | St. Goar et al. |
| 6,840,246 B2 | 1/2005 | Downing |
| 6,921,408 B2 | 7/2005 | Sauer |
| 6,978,176 B2 | 12/2005 | Lattouf |
| 6,991,635 B2 | 1/2006 | Takamoto et al. |
| 6,997,950 B2 | 2/2006 | Chawla |
| 7,112,207 B2 | 9/2006 | Allen et al. |
| 7,291,168 B2 | 11/2007 | Macoviak et al. |
| 7,294,148 B2 | 11/2007 | McCarthy |
| 7,309,086 B2 | 12/2007 | Carrier |
| 7,316,706 B2 | 1/2008 | Bloom et al. |
| 7,373,207 B2 | 5/2008 | Lattouf |
| 7,431,692 B2 | 10/2008 | Zollinger et al. |
| 7,513,908 B2 | 4/2009 | Lattouf |
| 7,534,260 B2 | 5/2009 | Lattouf |
| 7,608,091 B2 | 10/2009 | Goldfarb et al. |
| 7,618,449 B2 | 11/2009 | Tremulis et al. |
| 7,632,308 B2 | 12/2009 | Loulmet |
| 7,635,386 B1 | 12/2009 | Gammie |
| 7,666,196 B1 | 2/2010 | Miles |
| 7,744,609 B2 | 6/2010 | Allen et al. |
| 7,837,727 B2 | 11/2010 | Goetz |
| 7,871,368 B2 | 1/2011 | Zollinger et al. |
| 7,871,433 B2 | 1/2011 | Lattouf |
| 7,959,650 B2 | 6/2011 | Kaiser et al. |
| 8,029,518 B2 | 10/2011 | Goldfarb et al. |
| 8,029,565 B2 | 10/2011 | Lattouf |
| 8,043,368 B2 | 10/2011 | Crabtree |
| 8,147,542 B2 | 4/2012 | Maisano et al. |
| 8,187,323 B2 | 5/2012 | Mortier et al. |
| 8,226,711 B2 | 7/2012 | Mortier et al. |
| 8,241,304 B2 | 8/2012 | Bachman |
| 8,252,050 B2 | 8/2012 | Maisano et al. |
| 8,292,884 B2 | 10/2012 | Levine et al. |
| 8,303,622 B2 | 11/2012 | Alkhatib |
| 8,333,788 B2 | 12/2012 | Maiorino |
| 8,382,829 B1 | 2/2013 | Call et al. |
| 8,439,969 B2 | 5/2013 | Gillinov et al. |
| 8,454,656 B2 | 6/2013 | Tuval |
| 8,465,500 B2 | 6/2013 | Speziali |
| 8,475,525 B2 | 7/2013 | Maisano et al. |
| 8,500,800 B2 | 8/2013 | Maisano et al. |
| 8,608,758 B2 | 12/2013 | Singhatat et al. |
| 8,663,278 B2 * | 3/2014 | Mabuchi ........................ 606/139 |
| 8,771,296 B2 * | 7/2014 | Nobles ............... A61B 17/0469 606/144 |
| 8,828,053 B2 | 9/2014 | Sengun et al. |
| 8,852,213 B2 | 10/2014 | Gammie et al. |
| 9,131,884 B2 | 9/2015 | Holmes et al. |
| 2002/0013571 A1 | 1/2002 | Goldfarb et al. |
| 2003/0023254 A1 | 1/2003 | Chiu |
| 2003/0094180 A1 | 5/2003 | Benetti |
| 2003/0105519 A1 | 6/2003 | Fasol et al. |
| 2003/0120264 A1 | 6/2003 | Lattouf |
| 2003/0120341 A1 * | 6/2003 | Shennib ............... A61B 5/0215 623/2.12 |
| 2004/0044365 A1 | 3/2004 | Bachman |
| 2004/0093023 A1 | 5/2004 | Allen et al. |
| 2004/0143323 A1 | 7/2004 | Chawla |
| 2004/0199183 A1 | 10/2004 | Oz et al. |
| 2005/0004667 A1 | 1/2005 | Swinford et al. |
| 2005/0075654 A1 | 4/2005 | Kelleher |
| 2005/0119735 A1 | 6/2005 | Spence et al. |
| 2005/0149067 A1 | 7/2005 | Takemoto et al. |
| 2005/0149093 A1 | 7/2005 | Pokorney |
| 2005/0154402 A1 | 7/2005 | Sauer et al. |
| 2005/0216036 A1 | 9/2005 | Nakao |
| 2005/0216077 A1 | 9/2005 | Mathis et al. |
| 2005/0267493 A1 | 12/2005 | Schreck et al. |
| 2006/0100698 A1 | 5/2006 | Lattouf |
| 2006/0111739 A1 * | 5/2006 | Staufer ............ A61B 17/00234 606/192 |
| 2006/0167541 A1 | 7/2006 | Lattouf |
| 2006/0190030 A1 | 8/2006 | To et al. |
| 2007/0010857 A1 * | 1/2007 | Sugimoto et al. ............ 606/232 |
| 2007/0049952 A1 | 3/2007 | Weiss |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0149995 A1 * | 6/2007 | Quinn ............... A61B 17/12122 606/194 |
| 2007/0197858 A1 * | 8/2007 | Goldfarb ............ A61B 17/0401 600/37 |
| 2007/0213582 A1 | 9/2007 | Zollinger et al. |
| 2007/0270793 A1 | 11/2007 | Lattouf |
| 2008/0004597 A1 | 1/2008 | Lattouf et al. |

(56) References Cited

U.S. PATENT DOCUMENTS

| | | | |
|---|---|---|---|
| 2008/0009888 A1 | 1/2008 | Ewers et al. | |
| 2008/0140093 A1 | 6/2008 | Stone et al. | |
| 2008/0167714 A1 | 7/2008 | St. Goar et al. | |
| 2008/0188893 A1 | 8/2008 | Selvitelli et al. | |
| 2008/0228223 A1 | 9/2008 | Alkhatib | |
| 2008/0249504 A1 | 10/2008 | Lattouf et al. | |
| 2008/0269781 A1* | 10/2008 | Funamura | A61B 17/0401 606/138 |
| 2009/0005863 A1 | 1/2009 | Goetz et al. | |
| 2009/0043153 A1 | 2/2009 | Zollinger et al. | |
| 2009/0105729 A1 | 4/2009 | Zentgraf | |
| 2009/0105751 A1 | 4/2009 | Zentgraf | |
| 2009/0276038 A1 | 11/2009 | Tremulis et al. | |
| 2010/0023056 A1 | 1/2010 | Johansson et al. | |
| 2010/0023117 A1 | 1/2010 | Yoganathan et al. | |
| 2010/0023118 A1 | 1/2010 | Medlock | |
| 2010/0042147 A1 | 2/2010 | Janovsky et al. | |
| 2010/0174297 A1 | 7/2010 | Speziali | |
| 2010/0179574 A1* | 7/2010 | Longoria | A61B 17/0401 606/151 |
| 2010/0210899 A1 | 8/2010 | Schankereli | |
| 2010/0298930 A1 | 11/2010 | Orlov | |
| 2011/0015476 A1 | 1/2011 | Franco | |
| 2011/0022083 A1 | 1/2011 | DiMatteo et al. | |
| 2011/0022084 A1* | 1/2011 | Sengun | A61B 17/0401 606/228 |
| 2011/0028995 A1* | 2/2011 | Miraki | A61B 17/0482 606/144 |
| 2011/0029071 A1 | 2/2011 | Zlotnick et al. | |
| 2011/0060407 A1 | 3/2011 | Ketai et al. | |
| 2011/0106106 A1 | 5/2011 | Meier | |
| 2011/0144743 A1 | 6/2011 | Lattouf | |
| 2011/0264208 A1* | 10/2011 | Duffy et al. | 623/2.37 |
| 2011/0270278 A1* | 11/2011 | Overes | A61B 17/0057 606/144 |
| 2011/0288637 A1 | 11/2011 | De Marchena | |
| 2012/0004669 A1 | 1/2012 | Overes et al. | |
| 2012/0143215 A1 | 6/2012 | Carrao et al. | |
| 2012/0150223 A1 | 6/2012 | Manos et al. | |
| 2012/0179184 A1 | 7/2012 | Orlov | |
| 2012/0184971 A1 | 7/2012 | Zentgraf | |
| 2012/0203072 A1 | 8/2012 | Lattouf et al. | |
| 2012/0226294 A1 | 9/2012 | Tuval | |
| 2012/0226349 A1 | 9/2012 | Tuval et al. | |
| 2013/0018459 A1 | 1/2013 | Maisano et al. | |
| 2013/0035757 A1 | 2/2013 | Zentgraf et al. | |
| 2013/0253641 A1 | 9/2013 | Lattouf | |
| 2013/0282059 A1 | 10/2013 | Ketai et al. | |
| 2013/0345749 A1 | 12/2013 | Sullivan et al. | |
| 2014/0031926 A1 | 1/2014 | Kudlik et al. | |
| 2014/0039607 A1 | 2/2014 | Kovach | |
| 2014/0067052 A1 | 3/2014 | Chau et al. | |
| 2014/0214152 A1 | 7/2014 | Bielefeld | |
| 2014/0243968 A1 | 8/2014 | Padala | |
| 2014/0364938 A1 | 12/2014 | Longoria et al. | |
| 2015/0045879 A1 | 2/2015 | Longoria et al. | |

FOREIGN PATENT DOCUMENTS

| | | |
|---|---|---|
| WO | WO 2007/100268 | 9/2007 |
| WO | WO 2008/013869 | 1/2008 |
| WO | WO 2008/124110 | 10/2008 |
| WO | WO 2008/143740 | 11/2008 |
| WO | WO 2009/081396 | 7/2009 |
| WO | WO 2010/070649 | 6/2010 |
| WO | WO 2010/105046 | 9/2010 |
| WO | WO 2012/137208 | 10/2012 |
| WO | WO 2013/003228 | 1/2013 |
| WO | WO 2014/093861 | 6/2014 |
| WO | WO 2015/020816 | 2/2015 |

OTHER PUBLICATIONS

Office Action for U.S. Appl. No. 14/138,857, dated May 5, 2014, 12 pages.

International Search Report for International Application No. PCT/US2012/043761, dated Dec. 3, 2012.

International Preliminary Report on Patentability for International Application No. PCT/US2012/043761, dated Jan. 16, 2014.

Alfieri, O. et al., "The double-orifice technique in mitral valve repair: a simple solution for complex problems," (2001) J. Thorac. Cardiovasc. Surg., 122(4):674-681.

Barbero-Marcial, M. et al., "Transxiphoid Approach Without Median Sternotomy for the Repair of Atrial Septal Defects," (1998) Ann. Thorac. Surg., 65(3):771-774.

Braunberger, E. et al., "Very long-term results (more than 20 years) of valve repair with Carpentier's techniques in nonheumatic mitral valve insufficiency," (2001) Circulation, 104:I-8-I-11.

David, T. E. et al., "Replacement of chordae tendineae with Gore-Tex sutures: a ten-year experience," (1996) J. Heart Valve Dis., 5(4):352-355.

David, T. E. et al., "Mitral valve repair by replacement of chordae tendineae with polytetrafluoroethylene sutures," (1991) J. Thorac. Cardiovasc. Surg., 101(3):495-501.

Doty, D. B. et al., "Full-Spectrum Cardiac Surgery Through a Minimal Incision: Mini-Sternotomy (Lower Half) Technique," (1998) Ann. Thorac. Surg., 65(2):573-577.

Duran, C. M. et al., "Techniques for ensuring the correct length of new mitral chords," (2003) J. Heart Valve Dis., 12(2):156-161.

Eishi, K. et al., "Long-term results of artificial chordae implantation in patients with mitral valve prolapse," (1997) J. Heart Valve Dis., 6(6):594-598.

Frater, R. W. M., "Anatomical rules for the plastic repair of a diseased mitral valve," (1964) Thorax, 19:458-464.

Frater, R. W. M. et al., "Chordal replacement in mitral valve repair," (1990) Circulation, 82(suppl. IV):IV-125-IV-130.

Huber, C. H. et al., "Direct Access Valve Replacement (DAVR)—are we entering a new era in cardiac surgery?" (2006) European Journal of Cardio-thoracic Surgery, 29:380-385.

Hvass, U. et al., "Papillary Muscle Sling: A New Functional Approach to Mitral Repair in Patients With Ischemic Left Ventricular Dysfunction and Functional Mitral Regurgitation," (2003) Ann. Thorac. Surg., 75:809-811.

Kasegawa, H. et al., "Simple method for determining proper length of artificial chordae in mitral valve repair," (1994) Ann. Thorac. Surg., 57(1):237-239.

Kobayashi, J. et al., "Ten-year experience of chordal replacement with expanded polytetrafluoroethylene in mitral valve repair," (2000) Circulation, 102(19 Suppl 3):Iii-30-Iii-34.

Kunzelman, K. et al., "Replacement of mitral valve posterior chordae tendineae with expanded polytetrafluoroethylene suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorac. Cardiovasc. Surg., 133(1): 247-249.

Maisano, F. et al., "The double-orifice technique as a standardized approach to treat mitral regurgitation due to severe myxomatous disease: surgical technique," (2000) European Journal of Cardio-thoracic Surgery, 17(3):201-205.

Merendino, K. A. et al., "The open correction of rheumatic mitral regurgitation and/or stenosis with special reference to regurgitation treated by posteromedial annuloplasty utilizing a pump-oxygenator," (1959) Annals of Surgery, 150(1):5-22.

Minatoya, K. et al., "Pathologic aspects of polytetrafluoroethylene sutures in human heart," (1996) Ann. Thorac. Surg., 61(3):883-887.

Mohty, D. et al., "Very long-term survival and durability of mitral valve repair for mitral valve prolapse," (2001) Circulation, 104:I-1-I-7.

Nigro, J. J. et al., "Neochordal repair of the posterior mitral leaflet," (2004) J. Thorac. Cardiovasc. Surg., 127(2):440-447.

(56) References Cited

OTHER PUBLICATIONS

Phillips, M. R. et al., "Repair of anterior leaflet mitral valve prolapse: chordal replacement versus chordal shmtening," (2000) Ann. Thorac. Surg., 69(1):25-29.
Russo, M. J. et al. "Transapical Approach for Mitral Valve Repair during Insertion of a Left Ventricular Assist Device," Hindawi Publishing Corporation, The Scientific World Journal, vol. 2013, Article ID 925310, [online], Retrieved from the internet: <URL: http://dx.doi.org/10.1155/2013/925310> Apr. 11, 2013, 4 pages.
Sarsam, M. A. I., "Simplified technique for determining the length of artificial chordae in mitral valve repair," (2002) Ann. Thorac. Surg., 73(5):1659-1660.
Savage, E. B. et al., "Use of mitral valve repair: analysis of contemporary United States experience reported to the society of thoracic surgeons national cardiac database," (2003) Ann. Thorac. Surg., 75:820-825.
Speziali, G. et al., "Correction of Mitral Valve Regurgitation by Off-Pump, Transapical Placement of Artificial Chordae Tendinae, Results of the European TACT Trial" AATS 93rd Annual Meeting 2013, www.aats.org, 26 pages.
Suematsu, Y. et al., "Three-dimensional echo-guided beating heart surgery without cardiopulmonary bypass: Atrial septal defect closure in a swine model," (2005) J. Thorac. Cardiovasc. Surg., 130:1348-1357.
Von Oppell, U. O. et al., "Chordal replacement for both minimally invasive and conventional mitral valve surgery using premeasured Gore-Tex loops," (2000) Ann. Thorac. Surg., 70(6):2166-2168.
Zussa, C., "Artificial chordae," (1995) J. Heart Valve Dis., 4(2):S249-S254.
Zussa, C. et al., "Artificial mitral valve chordae: experimental and clinical experience," (1990) Ann. Thorac. Surg., 50(3):367-373.
Zussa, C. et al., "Seven-year experience with chordal replacement with expanded polytetrafluoroethylene in floppy mitral valve," (1994) J. Thorac. Cardiovasc. Surg., 108(1):37-41.
Zussa, C. et al., "Surgical technique for artificial mitral chordae implantation," (1991) Journal of Cardiac Surgery, 6(4):432-438.
Supplementary European Search Report for European Application No. 12804880.8, dated Nov. 28, 2014, 6 pages.
Carpentier, Alain, "Cardiac valve surgery—the 'French correction'," The Journal of Thoracic and Cardiovascular Surgery, vol. 86, No. 3, Sep. 1983, 15 pages.
*Neochord, Inc.* v. *University of Maryland, Baltimore*, Case No. IPR2016-00208, Petition for Inter PartesReview of U.S. Pat. No. 7,635,386, dated Nov. 18, 2015, 65 pages.
*Neochord, Inc.* v. *University of Maryland, Baltimore*, Case No. IPR2016-00208, Declaration of Dr. Lishan Aklog, dated Nov. 17, 2015, 91 pages.
*Neochord, Inc.* v. *University of Maryland, Baltimore*, Case No. IPR2016-00208, Decision on Institution of Inter Panes Review,37 CFR §42.108, Paper 6, Entered May 24, 2016, 28 pages.
Office Action for U.S. Appl. No. 14/584,561, dated Oct. 14, 2016, 5 pages.

\* cited by examiner

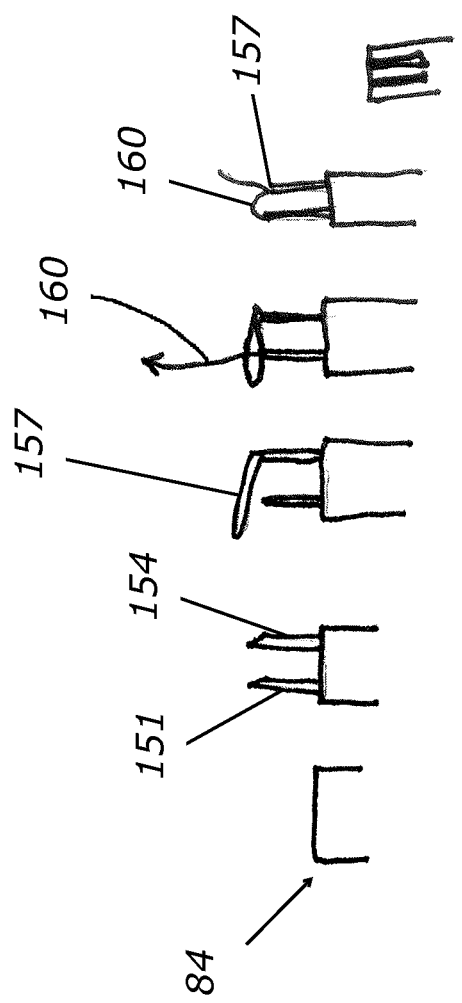

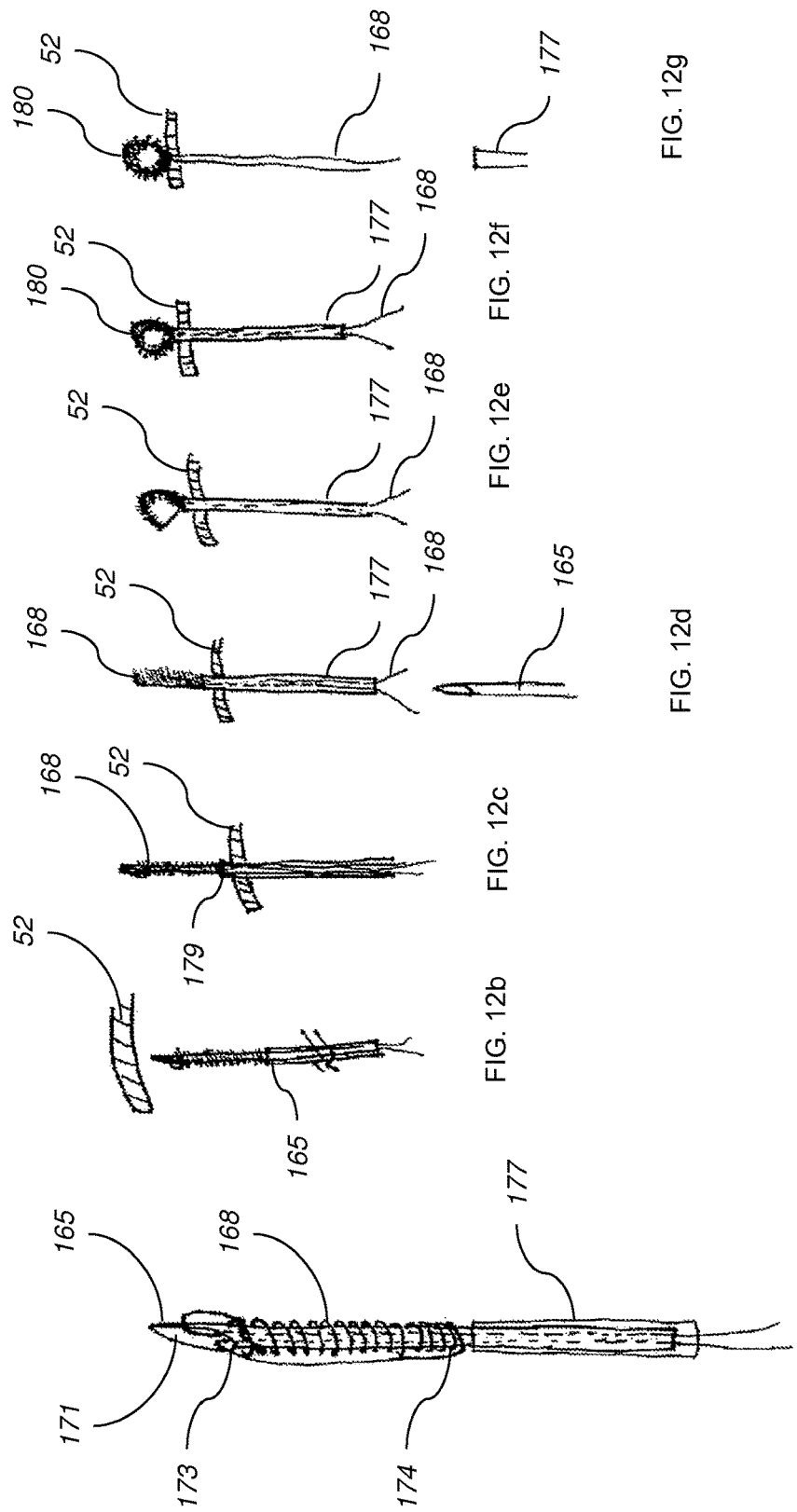

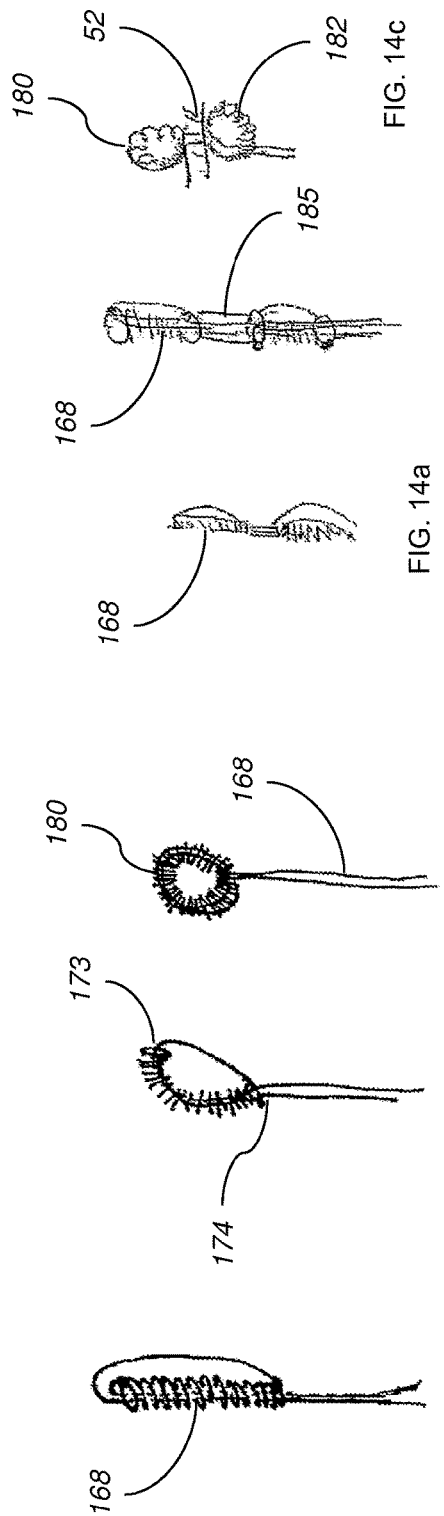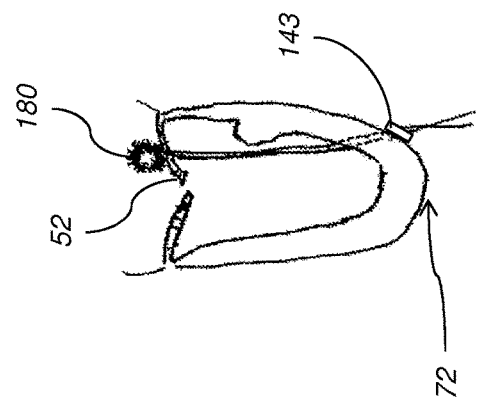

TRANSAPICAL MITRAL VALVE REPAIR METHOD

RELATED APPLICATIONS

This application is a divisional of and claims priority to U.S. patent application Ser. No. 14/138,857, filed Dec. 23, 2013 (now U.S. Pat. No. 8,852,213), entitled "Transapical Mitral Valve Repair Device," which is a continuation of and claims priority to International Application No. PCT/US2012/043761, filed Jun. 22, 2012, entitled "Transapical Mitral Valve Repair Device," which claims priority to and the benefit of U.S. Provisional Application No. 61/501,404, filed Jun. 27, 2011, entitled "Transapical Mitral Repair with Pre-Formed Knot," and U.S. Provisional Application No. 61/550,772, filed Oct. 24, 2011, entitled "Transapical Mitral Valve Repair Device," the disclosures of which are incorporated herein by reference in their entirety.

BACKGROUND

Field of the Disclosure

The disclosure herein relates to methods and devices for performing cardiac valve repairs, and more particularly, the disclosure relates to methods and devices for performing minimally invasive mitral or tricuspid valve repairs using of PTFE neochords through a minimally invasive incision, while the heart is beating.

Description of the Background

As illustrated in FIG. 1, the human heart 10 has four chambers, which include two upper chambers denoted as atria 12, 16 and two lower chambers denoted as ventricles 14, 18. A septum 20 divides the heart 10 and separates the left atrium 12 and left ventricle 14 from the right atrium 16 and right ventricle 18. The heart further contains four valves 22, 24, 26, and 28. The valves function to maintain the pressure and unidirectional flow of blood through the body and to prevent blood from leaking back into a chamber from which it has been pumped.

Two valves separate the atria 12, 16 from the ventricles 14, 18, denoted as atrioventricular valves. The left atrioventricular valve, the mitral valve 22, controls the passage of oxygenated blood from the left atrium 12 to the left ventricle 14. A second valve, the aortic valve 24, separates the left ventricle 14 from the aortic artery (aorta) 30, which delivers oxygenated blood via the circulation to the entire body. The aortic valve 24 and mitral valve 22 are part of the "left" heart, which controls the flow of oxygen-rich blood from the lungs to the body. The right atrioventricular valve, the tricuspid valve 26, controls passage of deoxygenated blood into the right ventricle 18. A fourth valve, the pulmonary valve 28, separates the right ventricle 18 from the pulmonary artery 32. The right ventricle 18 pumps deoxygenated blood through the pulmonary artery 32 to the lungs wherein the blood is oxygenated and then delivered to the left atrium 12 via the pulmonary vein. Accordingly, the tricuspid valve 26 and pulmonic valve 28 are part of the "right" heart, which control the flow of oxygen-depleted blood from the body to the lungs.

Both the left and right ventricles 14, 18 constitute "pumping" chambers. The aortic valve 24 and pulmonic valve 28 lie between a pumping chamber (ventricle) and a major artery and control the flow of blood out of the ventricles and into the circulation. The aortic valve 24 and pulmonic valve 28 have three cusps, or leaflets, that open and close and thereby function to prevent blood from leaking back into the ventricles after being ejected into the lungs or aorta 30 for circulation.

Both the left and right atria 12, 16 are "receiving" chambers. The mitral valve 22 and tricuspid valve 26, therefore, lie between a receiving chamber (atrium) and a ventricle so as to control the flow of blood from the atria to the ventricles and prevent blood from leaking back into the atrium during ejection into the ventricle. Both the mitral valve 22 and tricuspid valve 26 include two or more cusps, or leaflets (shown in FIG. 2), that are encircled by a variably dense fibrous ring of tissues known as the annulus. The valves are anchored to the walls of the ventricles by chordae tendineae (chordae) 42. The chordae tendineae 42 are cord-like tendons that connect the papillary muscles 44 to the leaflets (not shown) of the mitral valve 22 and tricuspid valve 26 of the heart 10. The papillary muscles 44 are located at the base of the chordae 42 and are within the walls of the ventricles. They serve to limit the movements of the mitral valve 22 and tricuspid valve 26 and prevent them from being reverted. The papillary muscles 44 do not open or close the valves of the heart, which close passively in response to pressure gradients; rather, the papillary muscles 44 brace the valves against the high pressure needed to circulate the blood throughout the body. Together, the papillary muscles 44 and the chordae tendineae 42 are known as the subvalvular apparatus. The function of the subvalvular apparatus is to keep the valves from prolapsing into the atria when they close.

As illustrated with reference to FIG. 2, the mitral valve 22 includes two leaflets, the anterior leaflet 52 and the posterior leaflet 54, and a diaphanous incomplete ring around the valve, called the annulus 60. The mitral valve 22 has two papillary muscles 44, the anteromedial and the posterolateral papillary muscles, which attach the leaflets 52, 54 to the walls of the left ventricle 14 via the chordae tendineae 42. The tricuspid valve 26 typically is made up of three leaflets with three papillary muscles. However, the number of leaflets can range between two and four. The three leaflets of the tricuspid valve 26 are referred to as the anterior, posterior, and septal leaflets. Although both the aortic and pulmonary valves each have three leaflets (or cusps), they do not have chordae tendineae.

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease), and infectious processes (e.g., endocarditis). Additionally, damage to the ventricle from prior heart attacks (i.e., myocardial infarction secondary to coronary artery disease) or other heart diseases (e.g., cardiomyopathy) can distort the valve's geometry causing it to dysfunction. However, the vast majority of patients undergoing valve surgery, such as mitral valve surgery, suffer from a degenerative disease that causes a malfunction in a leaflet of the valve, which results in prolapse and regurgitation.

Generally, a heart valve may malfunction two different ways. One possible malfunction, valve stenosis, occurs when a valve does not open completely and thereby causes an obstruction of blood flow. Typically, stenosis results from buildup of calcified material on the leaflets of the valves causing them to thicken and thereby impairing their ability to fully open and permit adequate forward blood flow.

Another possible malfunction, valve regurgitation, occurs when the leaflets of the valve do not close completely thereby causing blood to leak back into the prior chamber. There are three mechanisms by which a valve becomes regurgitant or incompetent; they include Carpentier's type I, type II and type III malfunctions. A Carpentier type I malfunction involves the dilation of the annulus such that normally functioning leaflets are distracted from each other and fail to form a tight seal (i.e., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation, and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (Ma) or dilation of the ventricle (IIIb).

FIG. 3 illustrates a prolapsed mitral valve 22. As can be seen with reference to FIG. 3, prolapse occurs when a leaflet 52, 54 of the mitral valve 22 is displaced into the left atrium 12 during systole. Because one or more of the leaflets 52, 54 malfunction, the mitral valve 22 does not close properly, and, therefore, the leaflets fail to coapt. This failure to coapt causes a gap 63 between the leaflets 52, 54 that allows blood to flow back into the left atrium 12, during systole, while it is being ejected into the left ventricle 14. As set forth above, there are several different ways a leaflet may malfunction, which can thereby lead to regurgitation.

Although stenosis or regurgitation can affect any valve, stenosis is predominantly found to affect either the aortic valve 24 or the pulmonic valve 28, whereas regurgitation predominately affects either the mitral valve 22 or the tricuspid valve 26. Both valve stenosis and valve regurgitation increase the workload on the heart 10 and may lead to very serious conditions if left un-treated; such as endocarditis, congestive heart failure, permanent heart damage, cardiac arrest, and ultimately death. Since the left heart is primarily responsible for circulating the flow of blood throughout the body, malfunction of the mitral valve 22 or tricuspid valve 26 is particularly problematic and often life threatening. Accordingly, because of the substantially higher pressures on the left side of the heart, left-sided valve dysfunction is much more problematic.

Malfunctioning valves may either be repaired or replaced. Repair typically involves the preservation and correction of the patient's own valve. Replacement typically involves replacing the patient's malfunctioning valve with a biological or mechanical substitute. Typically, the aortic valve 24 and pulmonic valve 28 are more prone to stenosis. Because stenotic damage sustained by the leaflets is irreversible, the most conventional treatment for stenotic aortic and pulmonic valves is removal and replacement of the diseased valve. The mitral valve 22 and tricuspid valve 26, on the other hand, are more prone to deformation. Deformation of the leaflets, as described above, prevents the valves from closing properly and allows for regurgitation or back flow from the ventricle into the atrium, which results in valvular insufficiency. Deformations in the structure or shape of the mitral valve 22 or tricuspid valve 26 are often repairable.

Valve repair is preferable to valve replacement. Bioprosthetic valves have limited durability. Moreover, prosthetic valves rarely function as well as the patient's own valves. Additionally, there is an increased rate of survival and a decreased mortality rate and incidence of endocarditis for repair procedures. Further, because of the risk of thromboembolism, mechanical valves often require further maintenance, such as the lifelong treatment with blood thinners and anticoagulants. Therefore, an improperly functioning mitral valve 22 or tricuspid valve 26 is ideally repaired, rather than replaced. However, because of the complex and technical demands of the repair procedures, the overall repair rate in the United States is only around 50%.

Conventional techniques for repairing a cardiac valve are labor-intensive, technically challenging, and require a great deal of hand-to-eye coordination. They are, therefore, very challenging to perform, and require a great deal of experience and extremely good judgment. For instance, the procedures for repairing regurgitating leaflets may require resection of the prolapsed segment and insertion of an annuplasty ring so as to reform the annulus of the valve. Additionally, leaflet sparing procedures for correcting regurgitation are just as labor-intensive and technically challenging, if not requiring an even greater level of hand-to-eye coordination. These procedures involve the implantation of sutures (e.g., ePTFE or GORE-TEXT™ sutures) so as to form artificial chordae in the valve. In these procedures, rather than performing a resection of the leaflets and/or implanting an annuplasty ring into the patient's valve, the prolapsed segment of the leaflet is re-suspended using artificial chord sutures. Oftentimes, leaflet resection, annuplasty, and neochord implantation procedures are performed in conjunction with one another.

Regardless of whether a replacement or repair procedure is being performed, conventional approaches for replacing or repairing cardiac valves are typically invasive open-heart surgical procedures, such as sternotomy or thoracotomy, that require opening up of the thoracic cavity so as to gain access to the heart. Once the chest has been opened, the heart is bypassed and stopped. Cardiopulmonary bypass is typically established by inserting cannulae into the superior and inferior vena cavae (for venous drainage) and the ascending aorta (for arterial perfusion), and connecting the cannulae to a heart-lung machine, which functions to oxygenate the venous blood and pump it into the arterial circulation, thereby bypassing the heart. Once cardiopulmonary bypass has been achieved, cardiac standstill is established by clamping the aorta and delivering a "cardioplegia" solution into the aortic root and then into the coronary circulation, which stops the heart from beating. Once cardiac standstill has been achieved, the surgical procedure may be performed. These procedures, however, adversely affect almost all of the organ systems of the body and may lead to complications, such as strokes, myocardial "stunning" or damage, respiratory failure, kidney failure, bleeding, generalized inflammation, and death. The risk of these complications is directly related to the amount of time the heart is stopped ("cross-clamp time") and the amount of time the subject is on the heart-lung machine ("pump time").

Furthermore, the conventional methods currently being practiced for the implantation of the artificial chordae are particularly problematic. Because the conventional approach requires the heart to be stopped (e.g., via atriotomy) it is difficult to accurately determine, assess, and secure the appropriate chordal length. Since the valve will not function properly if the length of the artificial chordae is too long or too short, the very problem sought to be eradicated by the chordal replacement procedure may, in fact, be exacerbated. Using conventional techniques, it is very difficult to ensure that the chordae are of the correct length and are appropriately spaced inside the ventricle to produce a competent valve.

There is a significant need to perform mitral valve repairs using less invasive procedures while the heart is still beating. Accordingly, there is a continuing need for new procedures and devices for performing cardiac valve repairs, such as mitral and tricuspid valve repairs, which are less invasive, do not require cardiac arrest, and are less labor-intensive and technically challenging. Chordal replacement procedures and artificial chordae that ensure the appropriate chordal length and spacing so as to produce a competent valve are of particular interest. The methods and repair devices presented herein meet these needs.

SUMMARY

It is an object of the disclosure to provide a method and device to enable minimally invasive, beating-heart, mitral valve repair.

It is another object of the disclosure to provide an expansile element that can be inserted through a mitral valve leaflet, and which can be deployed above the valve leaflet in order to secure it in place.

It is another object of the disclosure to enable chordal replacement with ePTFE. A related object of the present disclosure is to provide a chordal replacement that facilitates mitral valve repair.

Another object of the disclosure is to provide a method and device for transapical mitral valve repair that uses a small incision. A related object of the disclosure is to provide a method that does not require a Sternotomy. Another related object of the disclosure is to provide a method that does not require cardiopulmonary bypass or aortic manipulation.

Another object of the disclosure is to provide a method and device for transapical mitral valve repair that uses real-time, echo-guided, chordal length adjustment.

A basic concept of the method of the disclosure herein is to insert a tool via the apex of the heart, grasp or pierce the defective heart valve leaflet, deploy a PTFE neochord, and adjust the length of the chord under echo guidance to resolve the mitral valve regurgitation.

These and other objects of the present disclosure are accomplished by providing a device for minimally invasive repair of a defective heart valve while the heart is beating. The heart can be accessed through the apex or a point lateral/near to the apex with a small-diameter shafted instrument. The instrument might be a needle or a catheter. Using ultrasound guidance (real-time transesophagael echocardiography), the shafted instrument is inserted through an access port at the apex (or near the apex) and the instrument is guided to make contact with the mitral valve leaflet at the location where the operator has decided that a neochord should be inserted. Typically, this would be the body of the anterior or posterior leaflet in a location where the valve has prolapsed as a result of a broken or elongated chord. The instrument punctures the apex of the heart and travels through the ventricle. The tip of the instrument rests on the defective valve and punctures the valve leaflet. The instrument then inserts either a suture or a suture/guide wire combination, securing the top of the leaflet to the apex of the heart with an artificial chordae. A resilient element or shock absorber mechanism adjacent to the outside of the apex of the heart minimizes the linear travel of the instrument in response to the beating of the heart or opening/closing of the valve.

In a first embodiment, the instrument punctures the defective leaflet twice. A first needle deploys a loop wire with the loop encircling the area immediately above a second needle. The second needle deploys a suture through the loop deployed by the first needle. After the loop ensnares the suture, the loop and suture are retracted into the first needle. The instrument is pulled out of the heart while the suture remains through the leaflet. The length of the suture is adjusted and the ends of the suture are then affixed to the outer surface of the heart near the apex of the heart. Typically, the suture would be secured to a pledget.

According to another embodiment, once the instrument is in contact with the mitral valve leaflet in the targeted location, a "PTFE-wrapped needle" is advanced rapidly across the leaflet and subsequently rapidly withdrawn. After the PTFE-wrapped needle is advanced across the leaflet, the core is withdrawn and a pusher needle/sheath remains across the needle. Withdrawal pressure is applied to the two ends of the PTFE suture at the base of the needle (outside of the heart). This withdrawal pressure results in the development of a pre-formed knot that attains a significant size in the atrium, above the leaflet. The pusher needle is then withdrawn with the delivery instrument, and the length of the PTFE sutures are adjusted so that the amount of mitral regurgitation is minimized. Once this length is determined, the PTFE is secured to the outer surface of the heart using a pledget.

In another embodiment, a single needle punctures the defective leaflet and deploys a coated, coiled guide wire having a suture woven through it. The suture is then pulled, causing the guide wire to configure into a predetermined shape above the leaflet. The instrument is then retracted out of the heart and the length of the guide wire/suture is adjusted. Once this length is determined, the guide wire/suture is affixed near the apex of the heart.

BRIEF DESCRIPTION OF THE DRAWINGS

The above and other features, aspects, and advantages of the present disclosure are considered in more detail, in relation to the following description of embodiments thereof shown in the accompanying drawings, in which:

FIGS. 8a-8f show exemplary stages of the tip portion of an instrument according to an embodiment herein.

FIGS. 12a-12g show an exemplary instrument according to another embodiment herein.

FIGS. 13a-13c illustrates formation of a bulk knot in accordance with an embodiment herein.

FIGS. 14a-14c show an additional embodiment herein.

FIG. 15 illustrates an installed chord in accordance with an embodiment herein.

DETAILED DESCRIPTION

Figure 1:
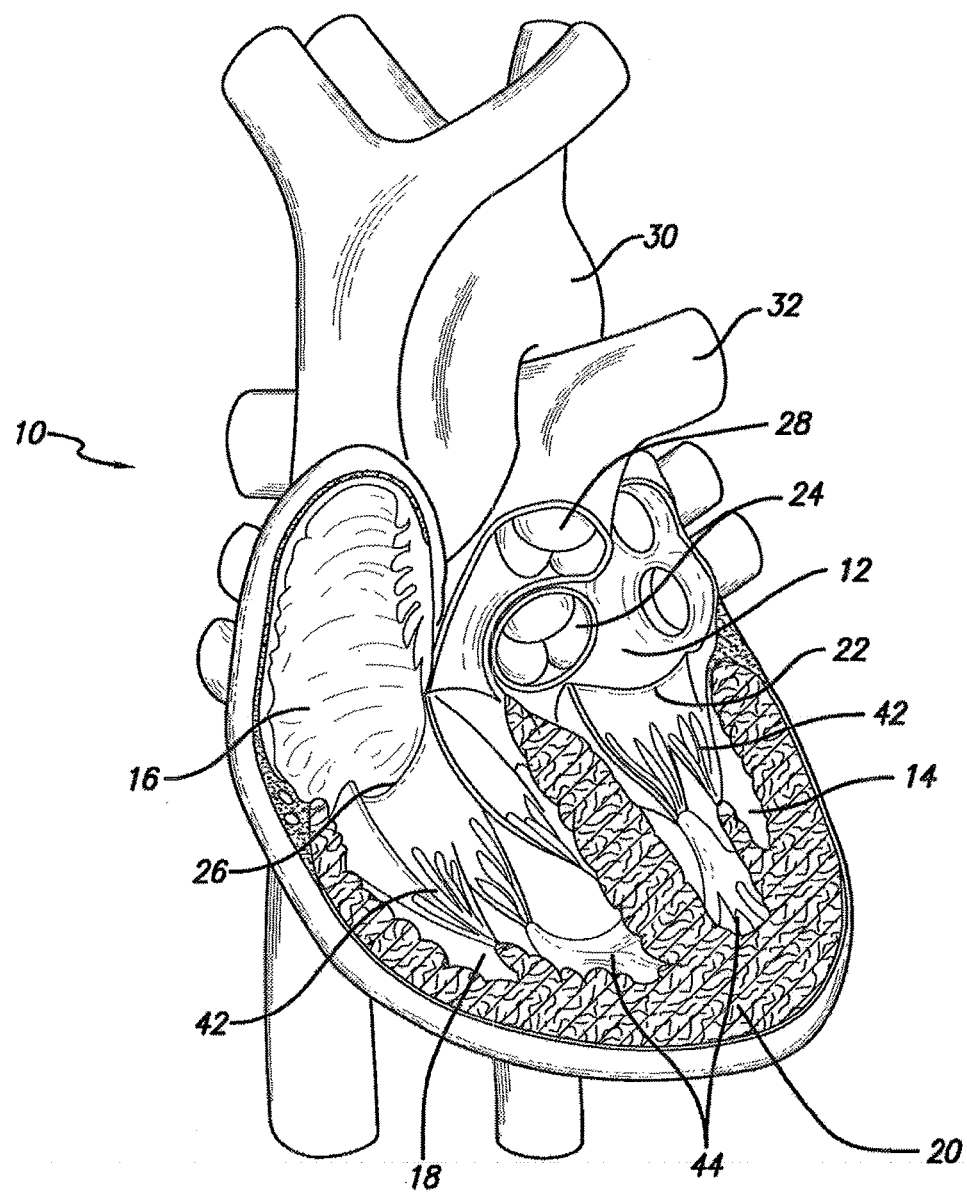
FIG. 1 is a cut-away anterior view of the human heart showing the internal chambers, valves, and adjacent structures.
Figure 2:
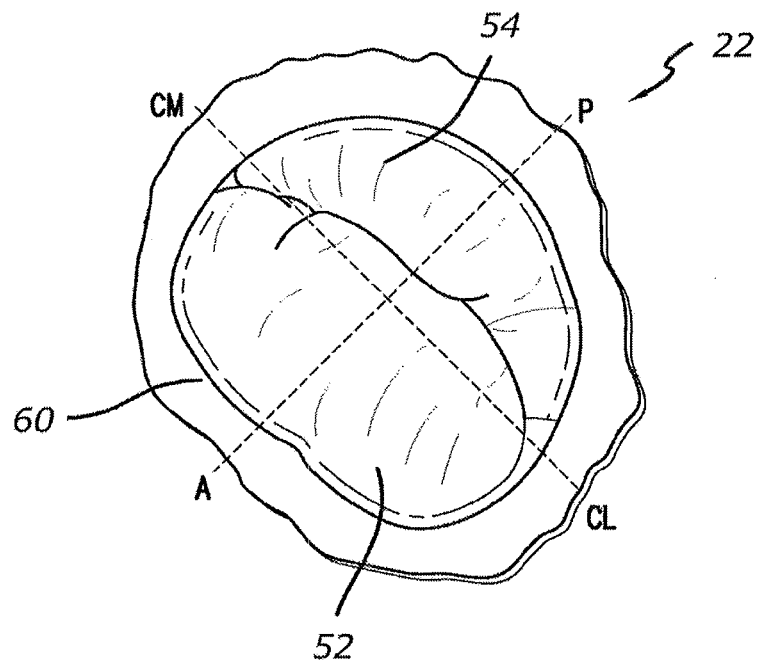
FIG. 2 is a perspective view of a healthy mitral valve with the leaflets closed.
Figure 3:
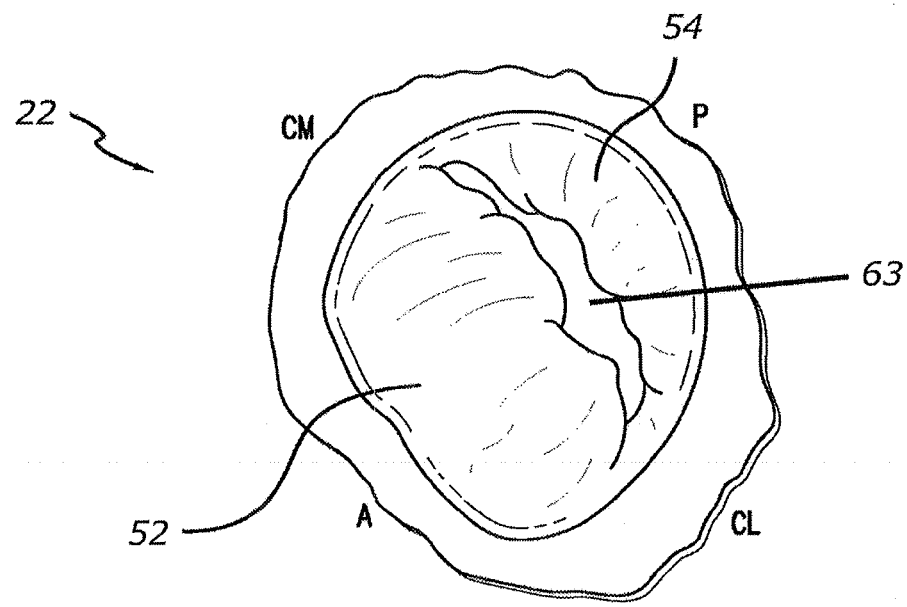
FIG. 3 is a top view of a dysfunctional mitral valve with a visible gap between the leaflets.

In accordance with the methods of embodiments herein, the heart may be accessed through one or more openings made by a small incision(s) in a portion of the body proximal to the thoracic cavity, for instance, in between one or more of the ribs of the rib cage, proximate to the xyphoid appendage, or via the abdomen and diaphragm. Access to the thoracic cavity may be sought so as to allow the insertion and use of one or more thorascopic instruments, while access to the abdomen may be sought so as to allow the insertion and use of one or more laparoscopic instruments. Insertion of one or more visualizing instruments may then be followed by transdiaphragmatic access to the heart. Additionally, access to the heart may be gained by direct puncture (i.e., via an appropriately sized needle, for instance an 18 gauge needle) of the heart from the xyphoid region. Access may also be achieved using percutaneous means. Accordingly, the one or more incisions should be made in such a manner as to provide an appropriate surgical field and access site to the heart. See for instance, Full-Spectrum Cardiac Surgery Through a Minimal Incision Mini-Sternotomy (Lower Half) Technique Doty et al. Annals of Thoracic Surgery 1998; 65(2): 573-7 and Transxiphoid Approach Without Median Sternotomy for the Repair of Atrial Septal Defects, Barbero-Marcial et al. Annals of Thoracic Surgery 1998; 65(3): 771-4 which are specifically incorporated in their entirety herein by reference.

After prepping and placing the subject under anesthesia a transesophageal echocardiogram (TEE) (2D or 3D), a transthoracic echocardiogram (TTE), intracardiac echo (ICE), or cardio-optic direct visualization (e.g., via infrared vision from the tip of a 7.5 F catheter) may be performed to assess the heart and its valves. A careful assessment of the location and type of dysfunction on the TEE, TTE, or other such instrument, facilitates the planning of the appropriate surgical procedure to be performed. The use of TEE, TTE, ICE, or the like, can assist in determining if there is a need for adjunctive procedures to be performed on the leaflets and subvalvular apparatus and can indicate whether a minimally invasive approach is advisable.

Once a minimally invasive approach is determined to be advisable, one or more incisions are made proximate to the thoracic cavity so as to provide a surgical field of access. The total number and length of the incisions to be made depend on the number and types of the instruments to be used as well as the procedure(s) to be performed. The incision(s) should be made in such a manner so as to be minimally invasive. By "minimally invasive" is meant in a manner by which an interior organ or tissue may be accessed with as little as possible damage being done to the anatomical structure through which entry is sought. Typically, a minimally invasive procedure is one that involves accessing a body cavity by a small incision made in the skin of the body. By "small incision" is meant that the length of the incision generally should be about 1 cm to about 10 cm, or about 4 cm to about 8 cm, or about 7 cm in length. The incision may be vertical, horizontal, or slightly curved. If the incision is placed along one or more ribs, it should follow the outline of the rib. The opening should extend deep enough to allow access to the thoracic cavity between the ribs or under the sternum and is preferably set close to the rib cage and/or diaphragm, dependent on the entry point chosen.

One or more other incisions may be made proximate to the thoracic cavity to accommodate insertion of a surgical scope. Such an incision is typically about 1 cm to about 10 cm, or about 3 cm to 7 cm, or about 5 cm in length and should be placed near the pericardium so as to allow ready access to and visualization of the heart. The surgical scope may be any type of endoscope, but is typically a thorascope or laparoscope, dependent upon the type of access and scope to be used. The scope generally has a flexible housing and at least a 16-times magnification. Insertion of the scope through an incision allows a practitioner to analyze and "inventory" the thoracic cavity and the heart so as to determine further the clinical status of the subject and plan the procedure. For example, a visual inspection of the thoracic cavity may reveal important functional and physical characteristics of the heart, and will indicate the access space (and volume) required at the surgical site and in the surgical field in order to perform the reparative cardiac valve procedure. At this point, the practitioner can confirm that access of one or more cardiac valves through the apex of the heart is appropriate for the particular procedure to be performed.

Figure 4:
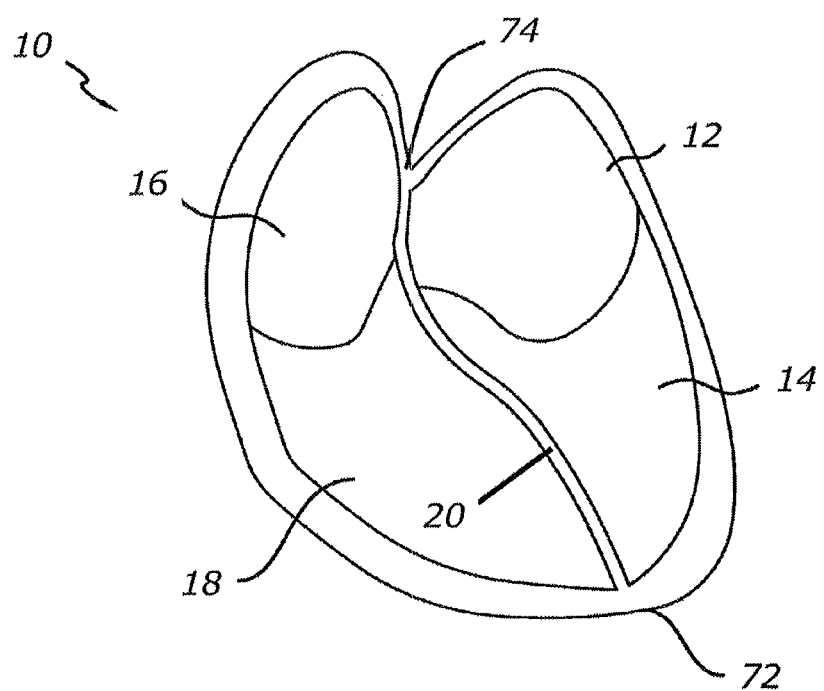
FIG. 4 shows a simplified view of a heart with four chambers and apex region.

With reference to FIG. 4, once a suitable entry point has been established, a suitable device such as one described herein, may be advanced into the body in a manner so as to make contact with the heart 10. The advancement of the device may be performed in conjunction with sonography or direct visualization (e.g., direct transblood visualization). For instance, the device may be advanced in conjunction with TEE guidance or ICE so as to facilitate and direct the movement and proper positioning of the device for contacting the appropriate apical region of the heart. Typical procedures for use of echo guidance are set forth in Suematsu, Y., J. Thorac. Cardiovasc. Surg. 2005; 130:1348-1356, herein incorporated by reference in its entirety.

One or more chambers 12, 14, 16, 18 in the heart 10 may be accessed in accordance with the methods disclosed herein. Access into a chamber in the heart may be made at any suitable site of entry but is preferably made in the apex region of the heart (e.g., at or adjacent to the apex 72). Typically, access into the left ventricle 14, for instance, to perform a mitral valve repair, is gained through making a small incision into the apical region, close to (or slightly skewed toward the left of) the median axis 74 of the heart 10. Typically, access into the right ventricle 18, for instance, to perform a tricuspid valve repair, is gained through making a small incision into the apical region, close to or slightly skewed toward the right of the median axis 74 of the heart 10. Generally, an apex region of the heart is a bottom region of the heart that is within the left or right ventricular region but is distal to the mitral valve 22 and tricuspid valve 26 and toward the tip or apex 72 of the heart 10. More specifically, an "apex region" of the heart is within a few centimeters to the right or to the left of the septum 20 of the heart 10. Accordingly, the ventricle can be accessed directly via the apex 72, or via an off apex location that is in the apical region, but slightly removed from the apex 72, such as via a lateral ventricular wall, a region between the apex and the base of a papillary muscle, or even directly at the base of a papillary muscle. Typically, the incision made to access the appropriate ventricle of the heart is no longer than about 1 mm to about 5 cm, from 2.5 mm to about 2.5 cm, from about 5 mm to about 1 cm in length.

As explained above, both the mitral valve 22 and tricuspid valve 26 can be divided into three parts—an annulus, leaflets, and a sub-valvular apparatus. If the valve is functioning properly, when closed, the free margins of the leaflets come together and form a tight junction the arc of which, in the mitral valve, is known as the line of coaptation. The normal mitral and tricuspid valves open when the ventricles relax allowing blood from the left atrium to fill the decompressed ventricle. When the ventricle contracts, the increase in pressure within the ventricle causes the valve to close, thereby preventing blood from leaking into the atrium and assuring that all of the blood leaving the ventricle is ejected through the aortic valve 24 and pulmonic valve 28 into the arteries of the body. Accordingly, proper function of the valves depends on a complex interplay between the annulus, leaflets, and subvalvular apparatus. Lesions in any of these components can cause the valve to dysfunction and thereby lead to valve regurgitation. As set forth above, regurgitation occurs when the leaflets do not coapt at peak contraction pressures. As a result, an undesired back flow of blood from the ventricle into the atrium occurs.

Once the malfunctioning cardiac valve has been assessed and the source of the malfunction verified, a corrective procedure can be performed. Various procedures can be performed in accordance with the methods of the disclosure herein in order to effectuate a cardiac valve repair, which will depend on the specific abnormality and the tissues involved.

In one embodiment, a method of the present disclosure includes the implantation of one or more artificial chordae tendineae into one or more leaflets of a malfunctioning mitral valve 22 and/or tricuspid valve 26. It is to be noted that, although the following procedures are described with reference to repairing a cardiac mitral or tricuspid valve by the implantation of one or more artificial chordae, the methods herein presented are readily adaptable for various types of leaflet repair procedures well-known and practiced in the art, for instance, an Alfieri procedure. In general, the methods herein will be described with reference to a mitral valve 22.

Figure 5:
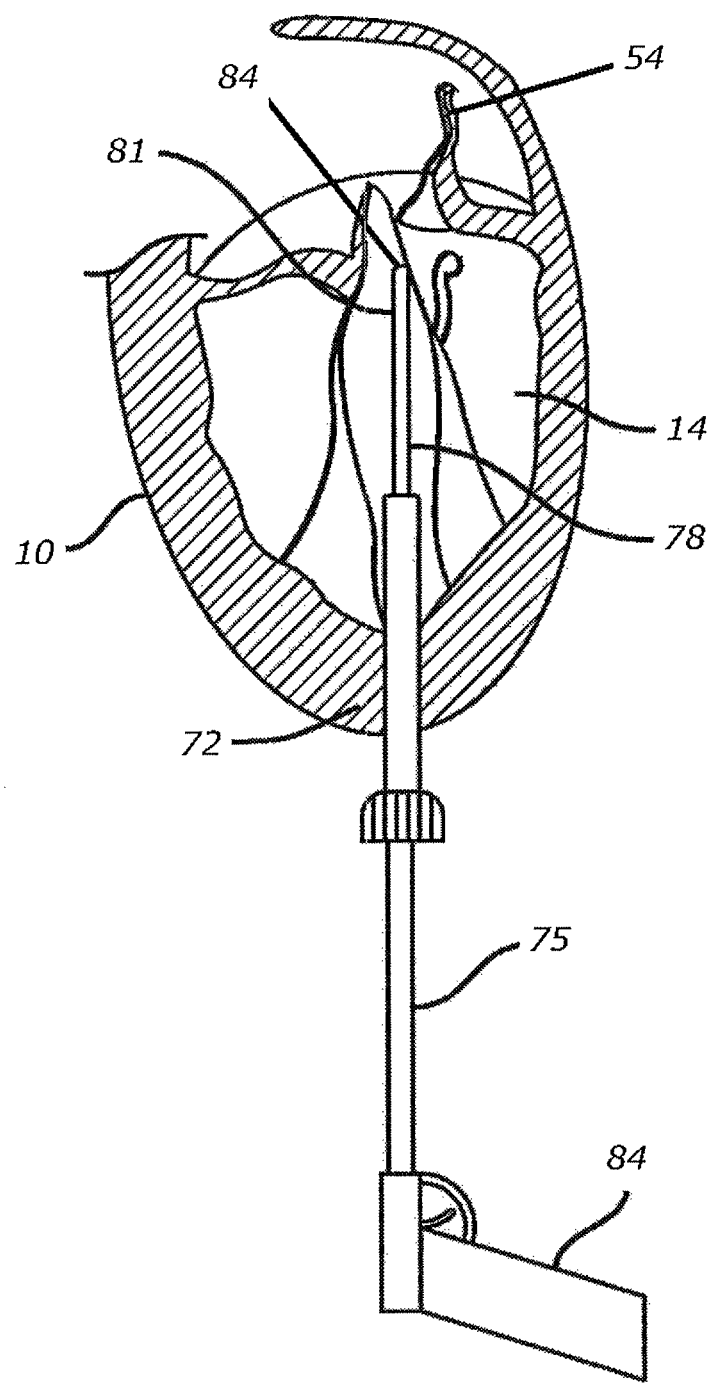
FIG. 5 illustrates the advancement of a device through an accessed region of the heart in accordance with the methods of embodiments herein.

As illustrated in FIG. 5, in accordance with the methods of the present disclosure, once an appropriate incision has been made in the apex region of the heart, for instance, in the apex 72, a suitable instrument 75 is then introduced into the ventricle 14 of the heart and advanced in such a manner so as to contact one or more cardiac tissues (for instance, a leaflet, an annulus, a cord, a papillary muscle, or the like) that are in need of repair. Sonic guidance, for instance, TEE guidance or ICE, may be used to assist in the advancement of the device into the ventricle and the grasping of the cardiac tissue with the device. Direct trans-blood visualization may also be used.

A suitable instrument 75, such as the one presented in FIGS. 5, 6a-6c, and 7, will typically include an elongate member 78 with a functional distal portion 81 having a tip 84 configured for repairing a cardiac valve tissue, for instance, a mitral valve leaflet 52, 54. The functional distal portion 81 of the device is configured for performing one or more selected functions, such as grasping, suctioning, irrigating, cutting, suturing, or otherwise engaging a cardiac tissue. Using a manipulatable handle portion 87, the instrument 75 is then manipulated in such a manner so that a selected cardiac tissue (for instance, a papillary muscle, one or more leaflet tissues, chordae tendineae, or the like) is contacted with the functional distal portion 81 of the instrument 75 and a repair effectuated, for instance, a mitral or tricuspid valve repair.

Figure 6A:
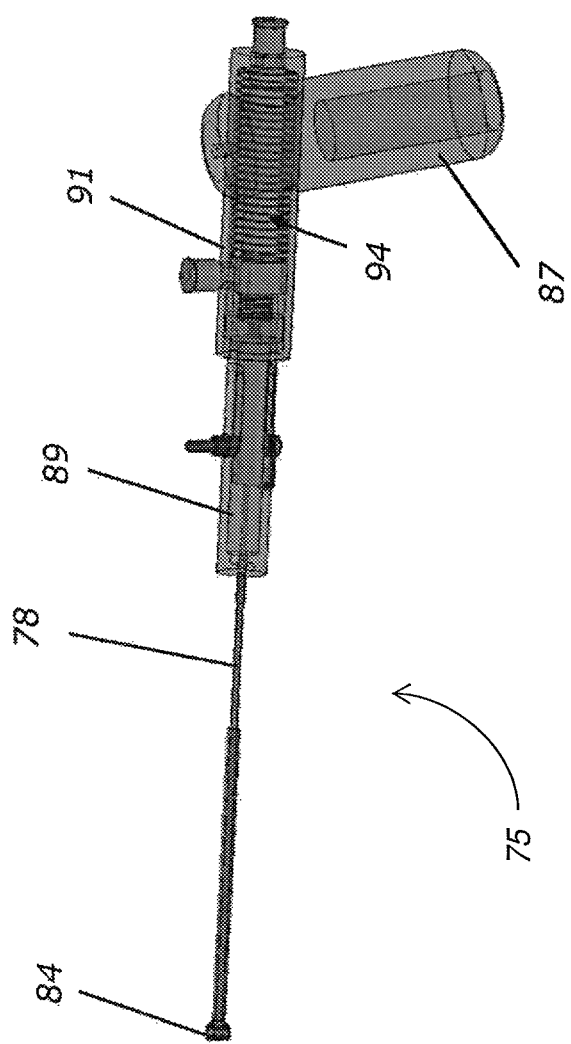
FIGS. 6a-6c illustrate an exemplary device according to embodiments herein.
Figure 6B:
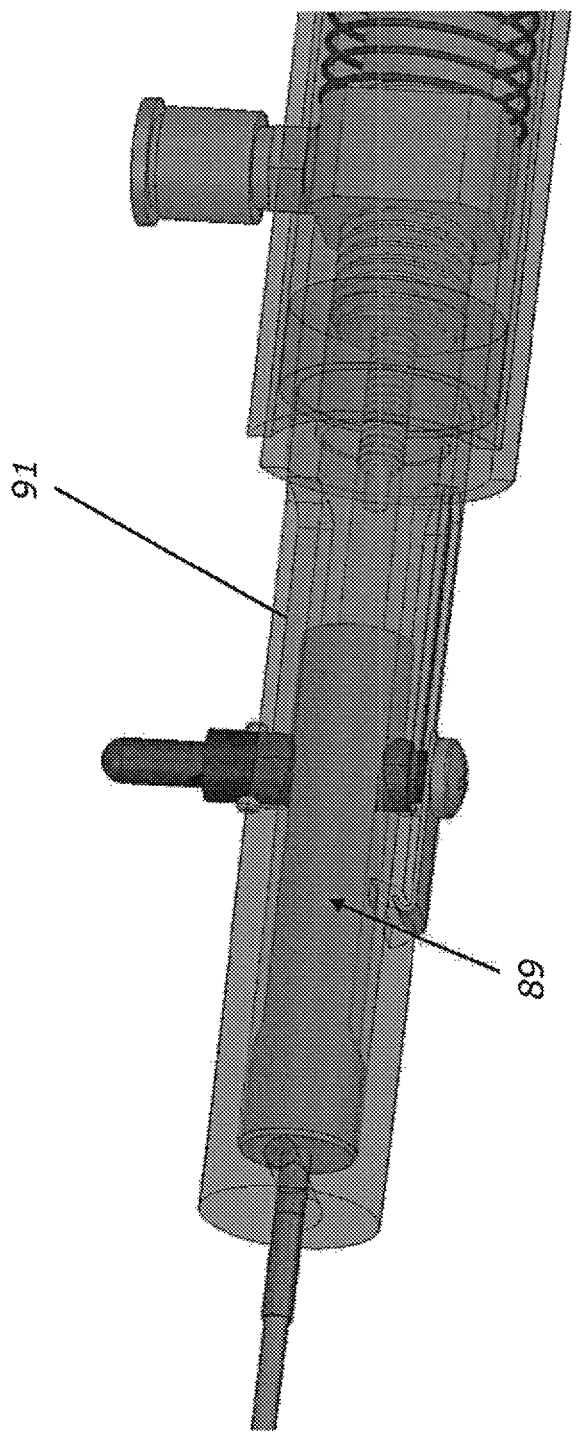
Figure 6C:
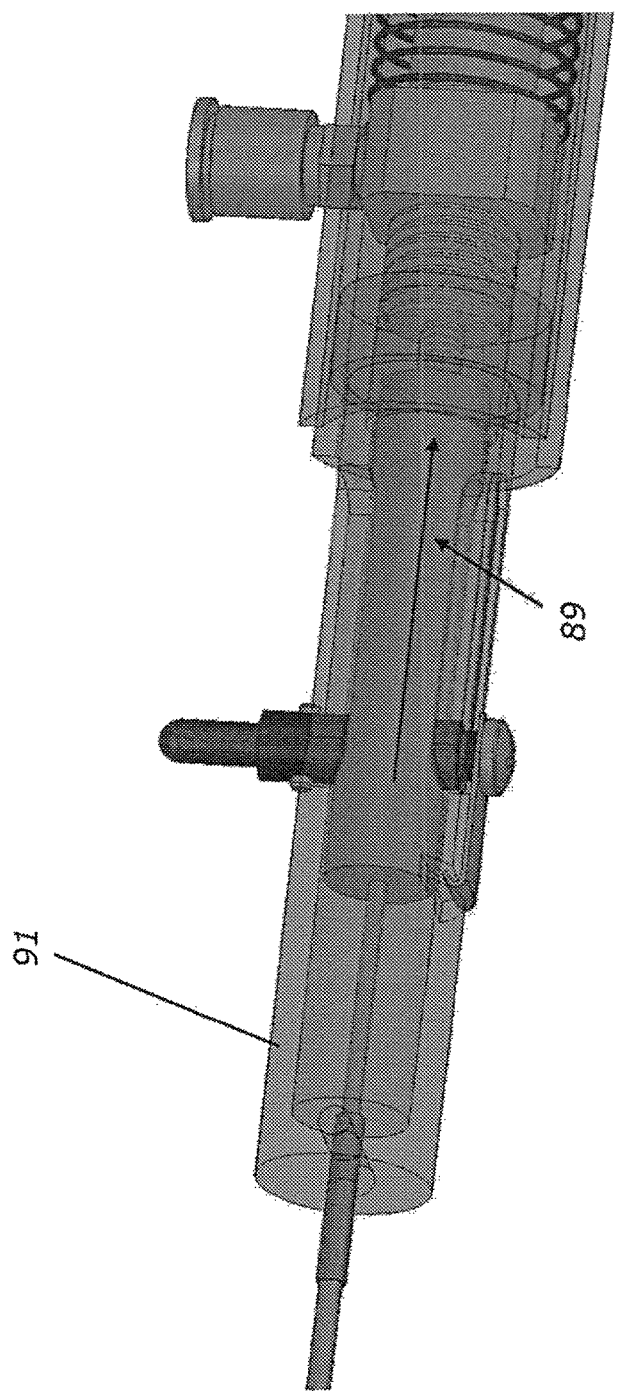

In one embodiment, the instrument 75 is designed to extend and contract with the beat of the heart. During systolic contraction, the median axis 74 of the heart 10 shortens. The distance from the apex 72 of the heart (where the device is inserted) to the mitral leaflet 52, 54 varies by 1-2 cm with each heartbeat. Accordingly, the instrument 75 is designed such that the tip 84 of the device (i.e. the part that contacts the mitral leaflet 52, 54) is "floating" wherein each systole is associated with approximately 1-2 cm of outward extension of the device. Referring to FIGS. 6a-6c, the instrument 75 includes an inner tube 89 and an outer tube 91. The inner tube 89 is configured to slide within the outer tube 91. A handle 87 is attached to the outer tube 91. A resilient element 94, such as a spring is present so that, as the outer tube 91 is advanced and the tip 84 makes contact with the leaflet 52, 54, the elongate portion 78, being connected to the inner tube 89, pushes against the resilient element 94. With forward pressure predetermined by the resilient element 94, once the tip 84 comes in contact with the leaflet 52, 54, even though the user continues to advance the instrument 75, the amount of pressure applied by the tip to the leaflet 52, 54 will remain constant as a result of the presence of the resilient element 94. The resilient element 94 allows a defined, constant forward force on the leaflet 52, 54. A user may feel contact, but will also be able to confirm visually that the resilient element 94 is extending and contracting.

Figure 7:
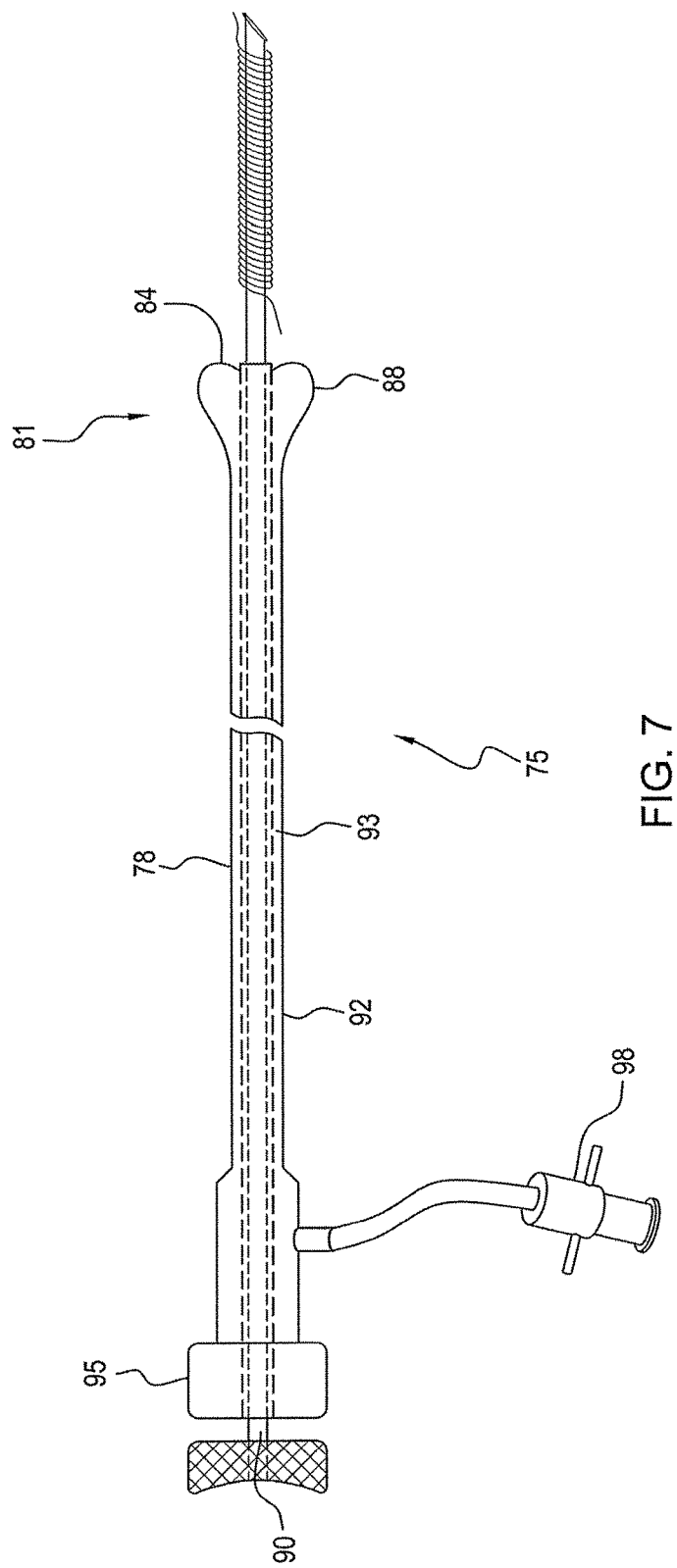
FIG. 7 illustrates an exemplary device according to embodiments herein.
Figure 9D:
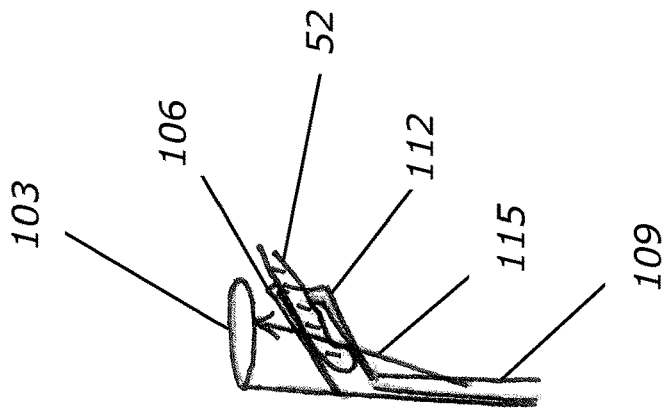
FIGS. 9a-9d show an exemplary instrument according to another embodiment herein.
Figure 9C:
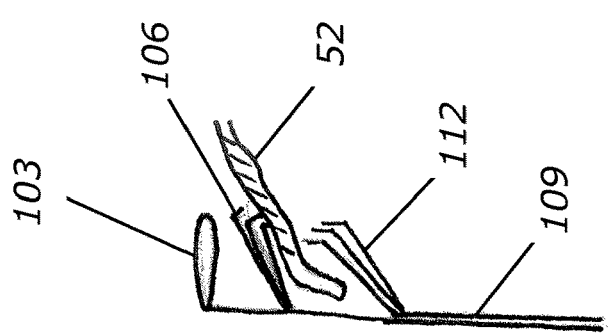
Figure 9B:
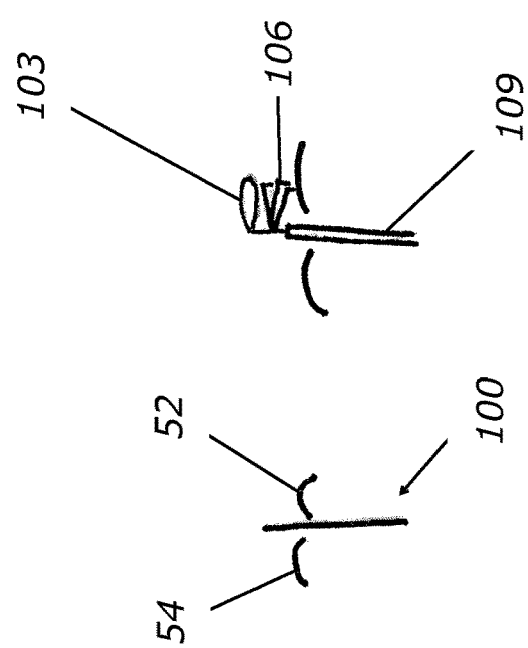
Figure 9A:
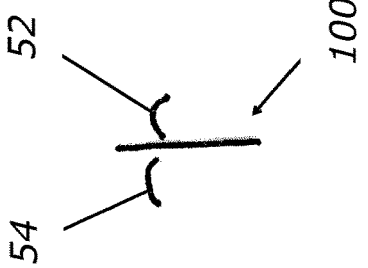
Figure 10D:
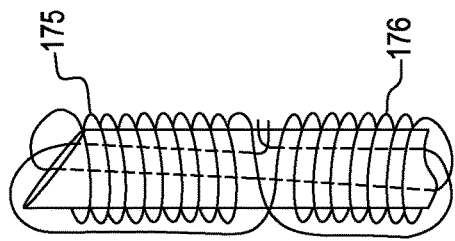
FIGS. 10a-10e illustrate an additional embodiment herein.
Figure 10C:
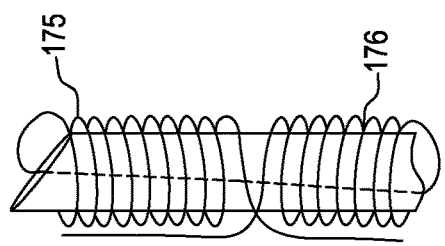
Figure 10B:
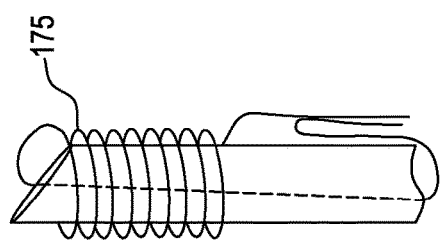
Figure 10E:
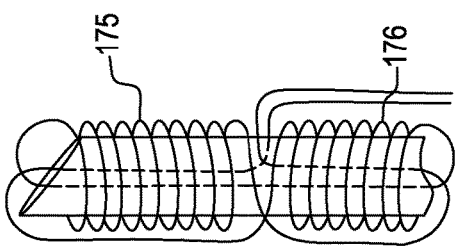
Figure 10A:
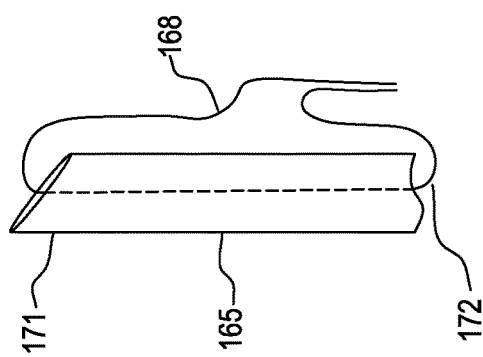

While a smaller seating surface enables the tip 84 to be more easily localized, it may be more likely to perforate the leaflet. A larger seating surface is more likely to remain in the selected location, but is harder to land on the leaflet 52, 54. Accordingly, in some embodiments, the delivery system may have a blunt end, to avoid pushing the entire device through the leaflet; to that end, a device with an expandable balloon 88 at the distal end, such as shown in FIG. 7, may be provided.

The inflatable balloon 88 is provided at the tip 84. The balloon 88 can distribute pressure more widely on the underside of the leaflet 52, 54, and minimize the likelihood that the leaflet will be perforated unintentionally by the device. Such a balloon 88 can be configured to surround the tip 84, thereby providing a broader seating surface against the leaflet. Once the instrument 75 is inserted, the balloon 88 can be inflated using methods known in the art. For example, the instrument 75 may include an inner lumen 90 comprising annealed stainless steel surrounded by an outer tube 92 made of urethane or other flexible material. A clearance space 93 between the inner lumen 90 and the outer tube 92 provides an inflation lumen. The outer tube should be bonded at one end around the tip 84 and at the other end to a valve 95, such as a Touhy valve. The valve 95 is tightened to the inner lumen 90. An inflation port 98 is provided to enable inflation of the balloon 88. In some embodiments, the balloon 88 may provide an expanded seating surface of approximately 6-7 mm.

Preferably, characteristics of the end surface of the tip 84 include ease of location on the leaflet, tendency to remain in one location, does not harm the leaflet by penetration, and can serve as a platform to deploy one or more needles, as described below.

FIGS. 8a-8f show exemplary stages of the tip portion 84 of an instrument 75 according to an embodiment of the present disclosure. In the embodiment illustrated in FIGS.

8a-8f, the tip 84 has two channels; each channel contains a needle. Preferably, one channel contains a larger needle, such as a 20-gauge and the other channel contains a smaller needle. It is not necessary that the needles be different sizes, nor is the needle gauge particular to the practice of this disclosure; other sizes may be used. In some embodiments, the snare described below could be a smaller gauge than the suture, allowing the needles to be the same size. Preferably, the two needles are as far apart as possible in the tip 84, so as to make the resulting suture that is installed less likely to tear the leaflet. In FIG. 8a, the needles are retracted. In FIG. 8b, both needles puncture the mitral valve leaflet (not shown); first the snare needle 151, then the suture needle 154. As shown in FIG. 8c, a metal (steel, nitinol, or other material) snare 157 is advanced through the larger needle. The snare 157 is adapted so that the loop can be selectively retracted or extended within the larger needle. The snare 157 is further adapted so that once it emerges (on the atrial side of the leaflet), it will deform in a predetermined manner, such as approximately a 90-degree bend, and is in position to capture a PTFE suture. While these steps may occur in rapid sequence, the snare 157 should not emerge until both needles have punctured the mitral valve leaflet. Preferably, the snare 157 includes a directional handle so that it is always deployed toward the center of the tip 84. FIG. 8d shows a PTFE suture 160 that is injected through the smaller needle (21 or 22 gauge) and passes through the deployed snare 157. Preferably, heparinized saline is used to inject the PTFE suture 160. As shown in FIG. 8e, the snare 157 is withdrawn into the 20-gauge needle, capturing the PTFE suture 160. In FIG. 8f, the device is removed, leaving a PTFE suture in the leaflet. An alternate approach would be to advance a metal guide wire through the smaller needle, grasp it, and pull it back. The PTFE suture could then be tied to the guide wire and pulled through.

FIG. 9 illustrates another embodiment using a "between the leaflets" approach for grasping and attaching a suture to a mitral valve leaflet 52, 54. In this embodiment, a shafted instrument 100 is inserted between two mitral valve leaflets 52, 54, as shown in FIG. 9a. FIG. 9b shows a snare 103 and a stiff "upper stabilizer" 106 deployed at the end of the instrument 100. Preferably, the snare 103 extends at approximately a 90-degree angle from the shaft 109. Typically, the upper stabilizer 106 will have an angle of approximately 70-80° from the shaft. A user then pulls the instrument 100 back until the upper stabilizer 106 lands on the mitral leaflet 52. Essentially, the leaflet 52 is stabilized by the shaft 109 (on the leading edge of the leaflet) and the snare stabilizer 106. Next, as shown in FIG. 9c, a second stabilizer (a narrow snare or prong) 112 is deployed below the leaflet 52. Typically, the second stabilizer 112 will have an angle of approximately 50-60° from the shaft. The second stabilizer 112 is progressively advanced toward the upper stabilizer 106. The leaflet 52 is "grabbed" by the two stabilizers 106, 112. Once the leaflet 52 is grasped, as shown in FIG. 9d, a needle 115 is ejected at an angle from the shaft 109. The needle 115 penetrates the leaflet 52, and passes through the upper stabilizer 106 and the snare 103. A PTFE suture is then injected through the needle 115 and captured by the snare 103. The needle 115 can then be retracted while the snare 103 holds the suture. Next, the snare 103 is withdrawn with the suture penetrating through the leaflet 52. The lower stabilizer 112 is withdrawn, followed by the upper stabilizer 106.

Figure 11:
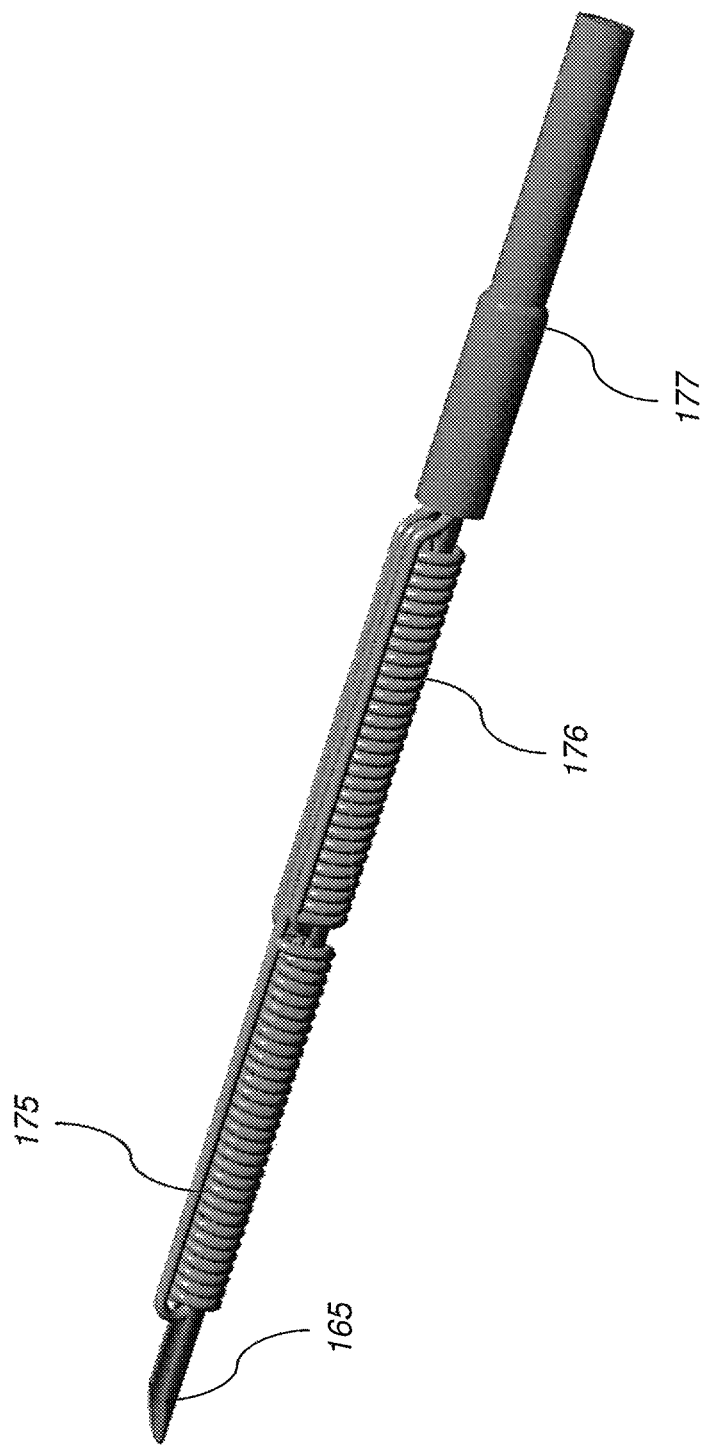
FIG. 11 shows an exemplary instrument according to an embodiment herein.

Another embodiment is shown in FIG. 10. A slotted needle 165 is wrapped with a PTFE suture. The needle 165 can be as small as 22 gauge. In some embodiments, the needle 165 may be electropolished to make it smooth. Referring to FIG. 10a, a suture 168 is prepared on the needle 165. Preferably, the suture is made of PTFE material. One end of the suture 168 emerges from a distal end 171 of the needle 165, and another end emerges from a slot 172. The suture 168 may have a simple knot 173 (see FIG. 12) where it emerges from the distal end 171 of the needle 165 and another knot at the end of the wrapping near the slot 172. In some embodiments, small, temporary silicone rings (not shown) may be used to hold the suture 168 at the distal and proximal ends. As shown in FIG. 10b, a first coil 175 is wound from the outside toward the inside (top to bottom). The suture 168 should wrapped tightly around the needle 165 for approximately 20-200 turns. Other numbers of turns may be used. As shown in FIG. 10c, a second coil 176 is wound from the outside toward the inside (bottom to top). Again, the suture 168 should be wrapped tightly around the needle 165 for approximately 20-200 turns. Other numbers of turns may be used. A short section may be left in the center for threading and completing the rest of the knot. The ends of the suture 168 may be crossed and looped from the end of the distal coil in the distal direction or in the direction of the proximal coil. The knot can be tightened by sliding the two coils 175, 176 to the center and twisting the coils to take up the slack in the needle slot, as shown in FIG. 10e. In some embodiments, a medical grade silicone may be used on the needle 165 and the wrapped suture 168 to allow smooth withdrawal of the needle 165 during subsequent procedure. FIG. 11 shows a finished version of a needle 165 with a suture 168 wrapped thereon.

Referring to FIG. 12, and particularly the portion labeled (a), the needle 165 has a suture 168 tightly wrapped around one end thereof. A pusher 177 or hollow guide wire may be provided on the needle 165. As shown in FIG. 12b, the wrapped needle 165 is inserted into the heart toward the mitral valve leaflet 52. The wrapped needle 165 can be advanced across the mitral valve leaflet 52 until the end of the wrapping, indicated by 179, is in the atrium above the leaflet 52, as shown in FIG. 12c, leaving a small hole. In FIG. 12d, the needle 165 is withdrawn, but the pusher 177 and suture 168 remain. In FIG. 12e, a withdrawal force applied to the ends of the suture 168 resulting in the transformation of the tightly wrapped coil of the suture 168 into a bulky knot 180 as shown in FIG. 12f. Lastly, as shown in FIG. 12g, the pusher 177 is withdrawn, leaving the permanent bulky knot 180, which anchors the suture 168 to the leaflet 52. In this embodiment, the resulting implant is made solely of a PTFE suture, which is a time-tested means of fixing the mitral valve.

There are many possible configurations of PTFE material and needle to form the bulky knot 180. For example, the suture 168 may form two or more loops, such as in FIG. 14. In some embodiments, the suture 168 may be double wrapped on the needle 165. Alternatively, the needle 165 may be non-hollow; that is, a solid needle. FIG. 13 illustrates how the simple bulky knot 180, described above, is formed. In FIG. 13a, the suture 168 is deployed. In FIG. 13b, the withdrawal force applied to the ends of the suture 168 pulls the knot 173 toward the end of the wrapping 174. Once the two ends meet, the bulky knot 180 remains, as shown in FIG. 13c.

In other words, according to the "bulky knot" concept: a PTFE suture 168 (or any kind of suture, or perhaps even a "filament") is wrapped tightly around a small-gauge needle 165, near the tip. The needle 165 is then advanced through the valve leaflet 52. A "pusher" 177 surrounds the needle 165 and extends to the level of the "wrap" of suture/filament.

Once the sharp point end of the needle and the wrap/coil of suture/filament 179 has passed through the leaflet 52, the needle 165 is withdrawn. This leaves the coil (s) 175, 176 unsupported. Tension on the ends of the filament/suture 168 at the base of the needle then cause a bulky knot 180 to form. Finally, the pusher 177 is pulled back, leaving a bulky knot 180 on the "far" side of the leaflet 52.

FIG. 14 illustrates an alternate embodiment of the bulky knot described above. An additional bulky knot 182 is created below the leaflet 52. The additional bulky knot 182 will sandwich the leaflet 52 between two knots. The distance between the knots should be no more than the thickness of the leaflet 52. As shown in FIG. 14b, a spacer 185 may be provided between the bulky knots 180, 182.

Referring to FIG. 15, once one or more bulky knots 180 have been implanted to one or more cardiac tissues, lengthening or shortening of the artificial chordae can be performed by knotting, tying, cutting, anchoring, and otherwise manipulating the cords in a manner so as to achieve the desired (e.g., optimal) length. Once the optimal length of the neochord is determined, the suture 168 can be tied off and/or anchored, outside of the apex 72, by any means well known in the art, for instance, by tying one or more knots into the suture 168. One or more pledgets 143 may also be used.

According to embodiments herein, the bulky knot concept can be used for an Alfieri stitch; that is, an Alfieri stitch can be created by sequentially deploying a double helix knot on first one leaflet of the mitral valve (i.e., the anterior leaflet 52), followed by the posterior leaflet 54, then tying the two together, using a knot pusher deployed from the apex 72.

Furthermore, while the embodiments disclosed herein are described with reference to a heart valve leaflet. The concepts are equally applicable to penetrating and applying similar knots to the annulus 60 of the valves. In some embodiments, several bulky knots 180 may be installed in the annulus 60 and tied together.

Figure 16:
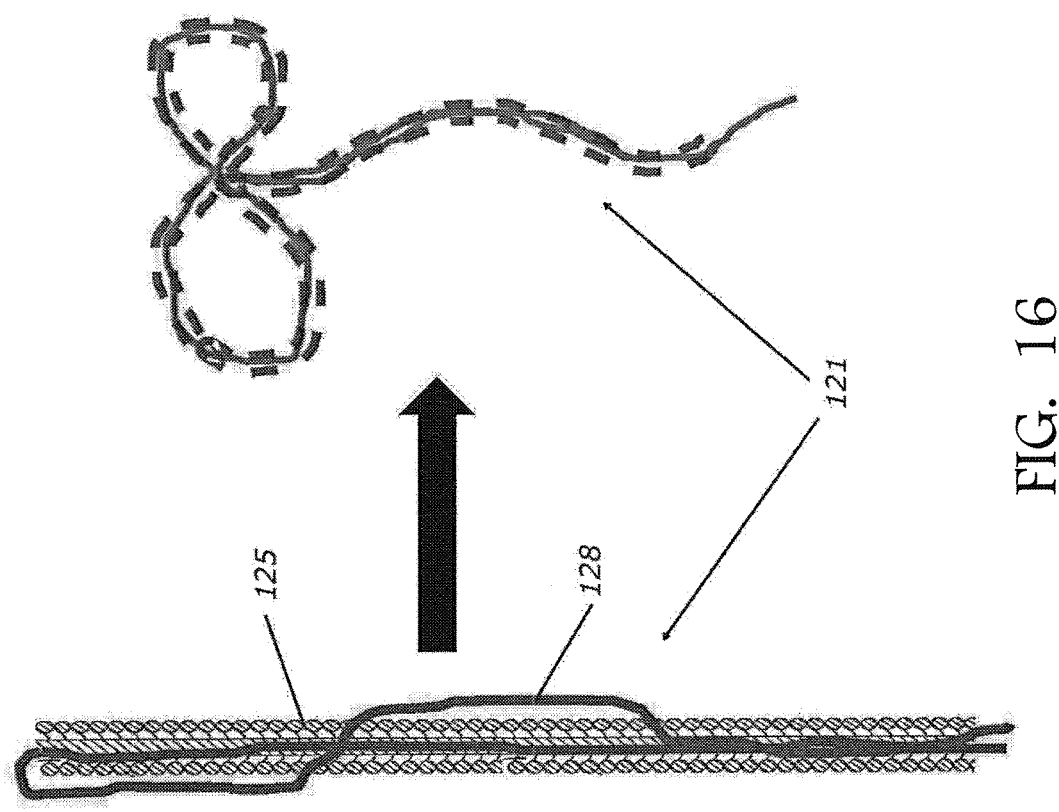
FIG. 16 illustrates an expansile element according to another embodiment herein.
Figure 17:
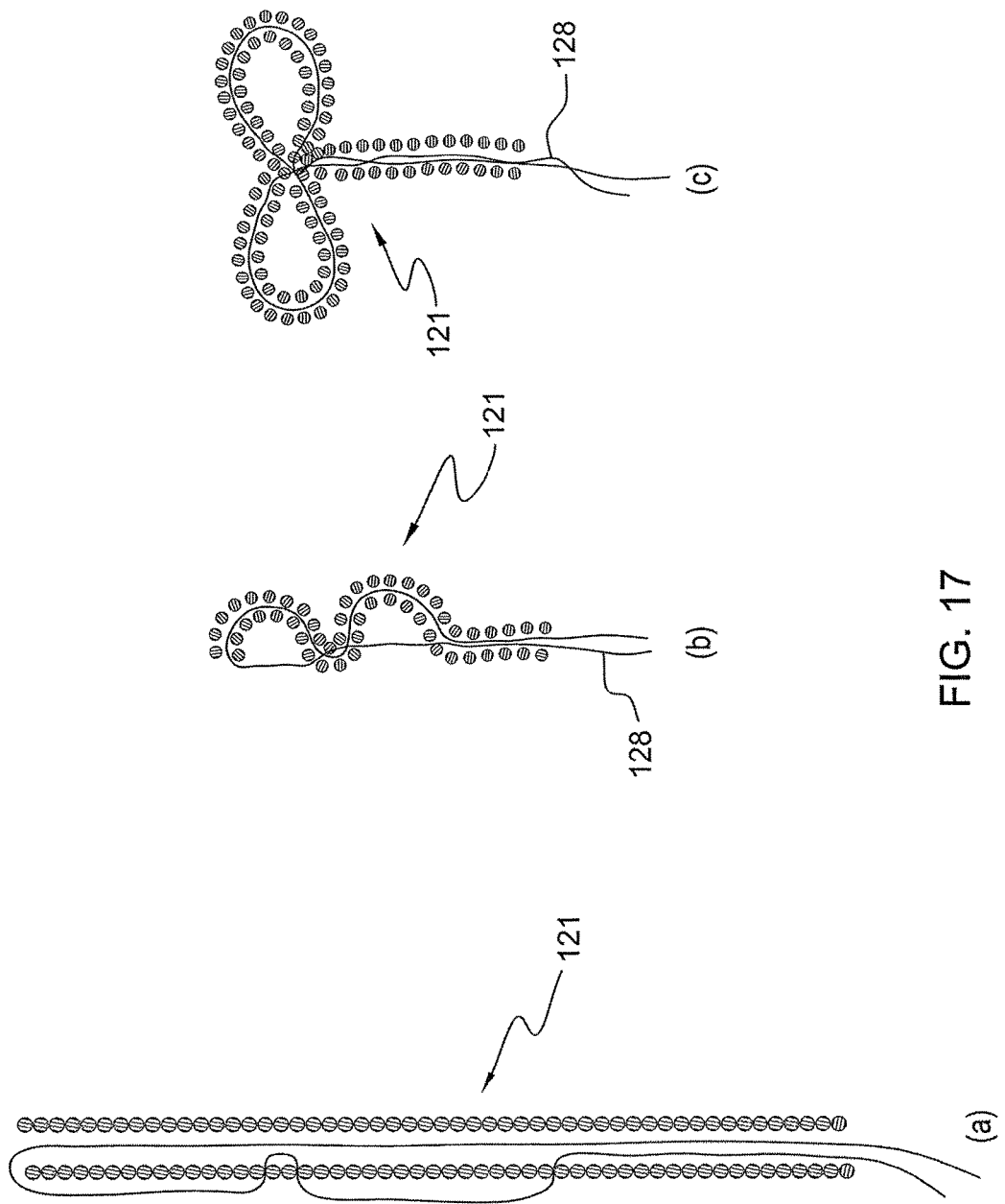
FIG. 17 is another illustration of an expansile element according to embodiments herein.

FIG. 16 shows another embodiment in which an expansile element 121 has been created. One approach for the expansile element 121 is a standard guide wire 125 made of an elongated spring formed of steel, nitinol, or other material. The guide wire 125 may be coated with PTFE or other appropriate coating. Alternatively, the guide wire 125 may remain uncoated. The guide wire 125 should be appropriately sized, such as 0.9 mm. Other sizes may be used. The expansile element 121 includes a suture 128 in the core. Preferably, the suture 128 is made of PTFE. The suture 128 is woven through the guide wire 125 as illustrated in FIG. 16 so that pulling on the suture 128 causes deformation of the tip of the expansile element 121 into a figure of 8 (or similar) configuration. FIG. 17 shows the progression of the expansile element 121 from an inactivated form as shown in FIG. 17a to a partially activated form in FIG. 17b, then to a fully activated form in FIG. 17c. The fully activated form may be in a spiral or helical shape or have one, two, three, or more loops, as desired.

Figure 18:
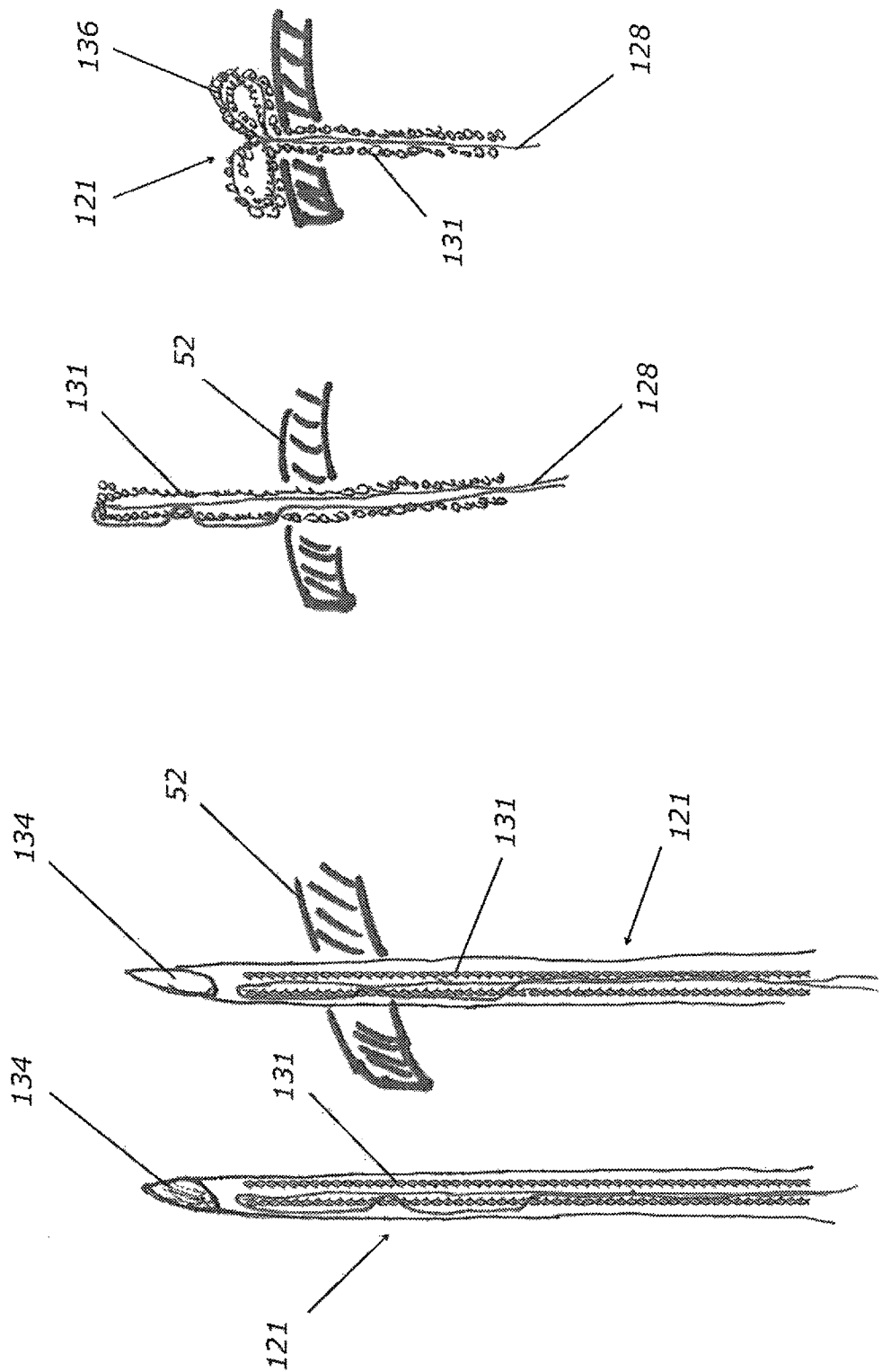
FIG. 18 illustrates use of a single needle device in accordance with the methods of embodiments herein.

Using an expansile element 121, a single-needle puncture procedure can be performed. As shown in FIG. 18, a neochord implant 131 that contains an expansile element 121 on the tip can be deployed once it has passed through the leaflet 52. The neochord implant 131 is inside an appropriately sized needle 134. The needle 134 may be 20-gauge, 19-gauge, 18-gauge, or other appropriate size. The needle 134 is used to penetrate the leaflet 52 and is then withdrawn, leaving the neochord implant 131 in place. The expansile element 121 is activated by pulling on the suture 128 causing deformation of the expansile element 121 at the tip into a predetermined configuration such as shown at 136, which keeps the implant 131 in place.

In some embodiments, the expansile element 121 may be self-forming; that is, the expansile element 121 can be made of a pre-shaped "memory" metal that is inserted into the needle 134. Withdrawal of the needle 134 allows the expansile element 121 to form its required shape.

Figure 19:
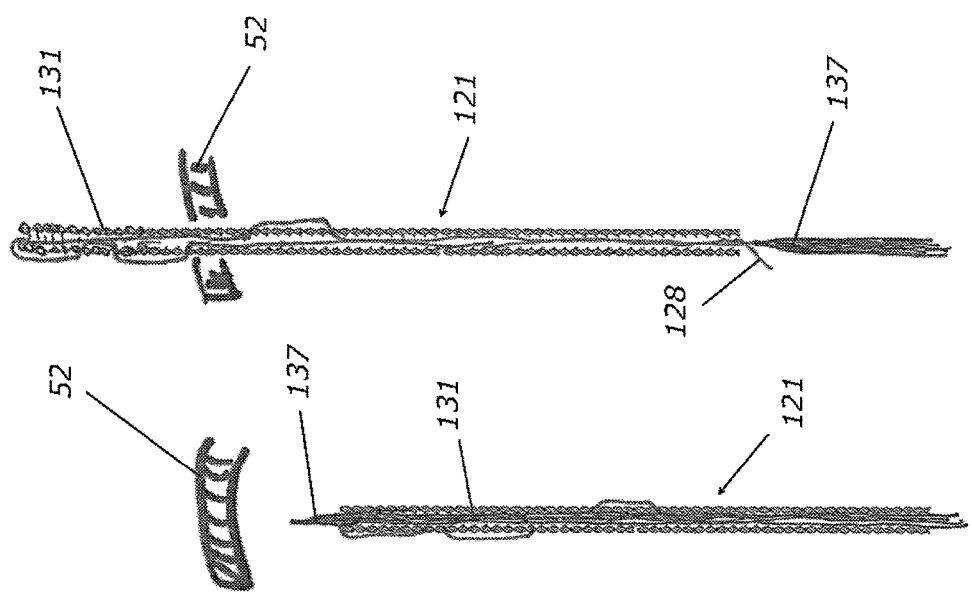
FIG. 19 illustrates use of an alternate single needle device in accordance with the methods of embodiments herein.

Alternatively, as shown in FIG. 19, an appropriately sized needle 137 or fine wire may be located inside the neochord implant 131. As above, the needle 137 is used to penetrate the leaflet 52 and is then withdrawn, leaving the neochord implant 131 in place. An advantage of having the needle 137 inside the implant 131 is that it enables tighter tolerance between the implant 131 and the leaflet 52. Additionally, if a fine wire is used, it could also be used to activate the expansile element 121 instead of the suture 128.

Figure 20:
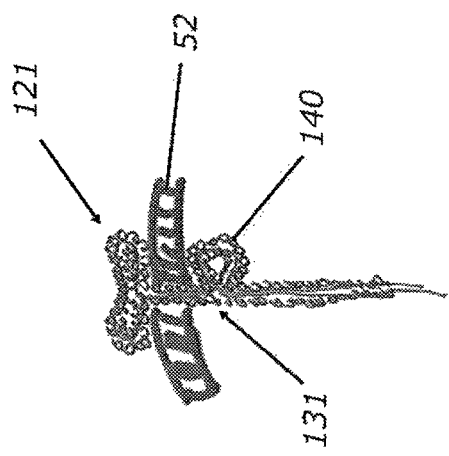
FIG. 20 shows an additional embodiment herein.

FIG. 20 shows an alternate configuration for the expansile element 121. An additional loop 140 is created below the leaflet 52. The additional loop 140 will sandwich the leaflet 52 between two loops of the implant 131. The distance between the loops should be no more than the thickest a leaflet 52 could be. As the additional loop 140 is formed, it will conform to the thickness of the leaflet 52.

Figure 21:
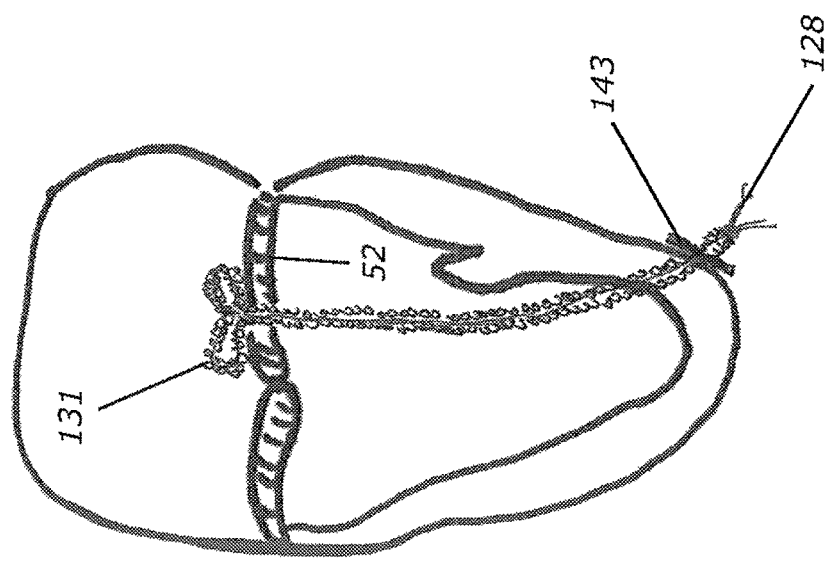
FIG. 21 illustrates locking steps in accordance with the methods of embodiments herein.

Referring to FIG. 21, once one or more implants 131 have been implanted to one or more cardiac tissues, the implantation device is removed through the access (e.g., via the access port), and the tail ends of the suture(s) 128 are trailed therethrough. Artificial chordae lengthening or shortening can be performed by knotting, tying, cutting, anchoring, and otherwise manipulating the cords in a manner so as to achieve the desired (e.g., optimal) length. Once the optimal length of the neochord is determined, the suture 128 can be tied off and/or anchored, outside of the apex 72, by any means well known in the art, for instance, by tying one or more knots into the suture 128. One or more pledgets 143 may also be used.

Figure 22:
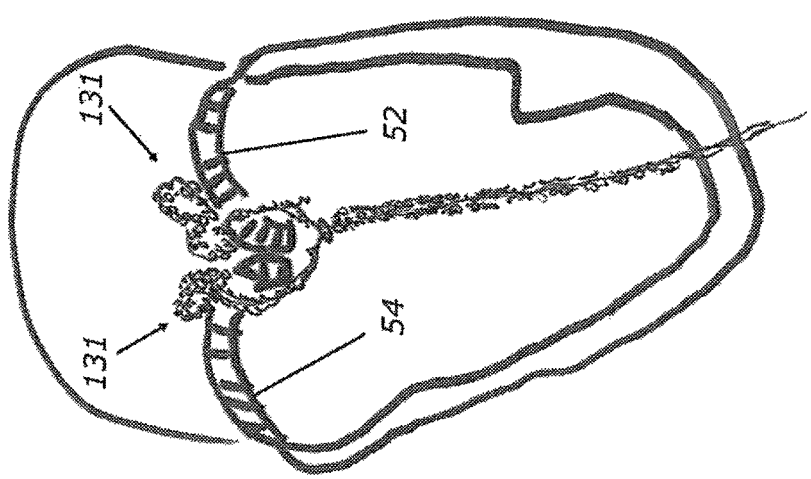
FIG. 22 illustrates use of the device of embodiments herein in accordance with another method.

In another approach, the neochord implant 131 of the present disclosure herein can be used in an edge-to-edge (Alfieri) repair, as shown in FIG. 22. A first implant 131 is deployed on one leaflet 52. A second implant 131 is deployed on the second leaflet 54. The two implants are then banded together to create adjoining edges.

The sutures that are to be implanted (for instance, so as to function as artificial chordae tenidinae or neochords) may be fabricated from any suitable material, such as but not limited to: polytetrafluoroethylene (PTFE), nylon, Gore-Tex, Silicone, Dacron, or the like. With respect to the implantation of artificial chordae, the particular function of the replacement cord is dependent upon the configuration, physical characteristics and relative positioning of the structure(s). In certain embodiments, the structures act to restrain the abnormal motion of at least a portion of one or more of the valve leaflets. In other embodiments, the prosthetic chordae provide a remodeling as well as a leaflet restraint function where the latter may address latent or residual billowing of the leaflet body and/or latent or residual prolapsing of the leaflet edge, either of which may result from the remodeling itself or from a physiological defect.

It is to be noted that a fundamental challenge in successfully replacing one or more chordae tendineae and restoring proper functioning of a cardiac valve, is determining the appropriate artificial cord length and securing the artificial cord at a location so as to ensure the optimal replacement chordae length. The valve will not function properly if the length of the artificial cord is too long or too short. Because the heart is stopped using conventional techniques, it is virtually impossible to ensure that the cords are of the correct length and are appropriately spaced inside the ventricle to produce a competent valve. Accordingly, methods of the disclosure herein include the measuring and determining of the optimal arrangement, length, placement, and configuration of an implanted suture, for instance, a replacement cord length, while the heart is still beating and, typically, before the access site of the heart is closed. An optimal arrangement of a suture, for instance, an optimal cord length, is that arrangement that effects said repair, for instance, by minimizing reperfusion as determined by means well known in the art, for instance, by direct echo guidance.

Therefore, in accordance with the methods of the disclosure herein, once one or more artificial chordae have been implanted to one or more cardiac tissues, the implantation device is removed through the access (e.g., via the access port), and as stated above, the tail ends of the suture(s) are trailed therethrough. The optimal length of the implanted suture(s) (i.e., neochord) can then be determined by manipulating the ends of the suture(s) in a graded and calibrated fashion that is akin to manipulating a marionette. The manipulation of the artificial chordae may be done in conjunction with audio or visual assistance means, for instance, direct echo (e.g., echocardiographic) guidance, by which the degree and extent of regurgitation can be measured while the chordal length is being manipulated, so as to determine a chordal length that minimizes any observed regurgitation. Since, in a preferred embodiment, the heart is still beating the degree of cardiac regurgitation can be evaluated real time and the optimal neochord(s) length determined. Accordingly, an optimal cord length is a cord length that is determined, for instance, by direct echo guidance, to minimize or at least reduce cardiac valve regurgitation. Artificial chordae lengthening or shortening can be performed, as described above, by knotting, tying, cutting, anchoring, and otherwise manipulating the cords in a manner so as to achieve the desired (e.g., optimal) length. Once the optimal length of the neochord is determined, the sutures can be tied off and/or anchored, outside of the apex, by any means well known in the art, for instance, by tying one or more knots into the suture. One or more pledgets may also be used.

Once the corrective procedures are completed, the repaired valve may be further assessed, and if the repair is deemed satisfactory, the one or more devices (e.g., cannulae, sheath, manifold, access port, etc.) are removed, the access closed, as described above, and the percutaneous incisions are closed in a fashion consistent with other cardiac surgical procedures. For instance, one or more purse-string sutures may be implanted at the access site of the heart and/or other access sites, so as to close the openings.

It is further contemplated that the devices and methods disclosed herein can be used in procedures outside the heart. That is, while the embodiments have been described with reference to a heart valve, the devices and methods described above may be used in any procedure that requires penetrating a tissue and forming a knot on the far side thereof.

The present disclosure has been described with references to specific embodiments. While particular values, relationships, materials and steps have been set forth for purposes of describing concepts of the disclosure herein, it will be appreciated by persons skilled in the art that numerous variations and/or modifications may be made to the disclosure herein as shown in the disclosed embodiments without departing from the spirit or scope of the basic concepts and operating principles of the disclosure herein as broadly described. It should be recognized that, in the light of the above teachings, those skilled in the art could modify those specifics without departing from the disclosure herein taught herein. Having now fully set forth certain embodiments and modifications of the concept underlying the present disclosure herein, various other embodiments as well as potential variations and modifications of the embodiments shown and described herein will obviously occur to those skilled in the art upon becoming familiar with such underlying concept. It is intended to include all such modifications, alternatives and other embodiments insofar as they come within the scope of the appended claims or equivalents thereof. It should be understood, therefore, that the disclosure herein might be practiced otherwise than as specifically set forth herein. Consequently, the present embodiments are to be considered in all respects as illustrative and not restrictive.

What is claimed is:

1. A method of repairing a prolapsed leaflet of a valve of a heart comprising:
    introducing into a ventricle of the heart a distal portion of a delivery system having a distal tip and carrying an artificial chordae having a distal portion and a proximal portion;
    disposing the distal tip of the delivery system in contact with a ventricular side of the leaflet;
    while maintaining the entire distal portion of the delivery system on the ventricular side of the leaflet, extending from the distal tip of the delivery system a needle having a distal portion carrying the distal portion of the artificial chordae to pierce a prolapsed segment of the leaflet from the ventricular side of the leaflet to an atrial side of the leaflet to form an opening in the leaflet;
    passing through the opening, from the ventricular side to the atrial side, the distal portion of the artificial chordae disposed in a first configuration, and with the proximal portion of the artificial chordae remaining on the ventricular side of the leaflet;
    causing the distal portion of the artificial chordae to change from the first configuration to a second configuration, the second configuration being larger than the opening in the leaflet;
    securing the artificial chordae to an apex region of the heart to reduce prolapse of the leaflet;
    the artificial chordae includes a medial portion between the distal portion of the artificial chordae and the proximal portion of the artificial chordae; and
    the passing through the opening includes the medial portion of the artificial chordae disposed in a first configuration remaining on the ventricular side of the leaflet, and
    further comprising causing the medial portion of the artificial chordae to change from the first configuration of the artificial chordae to a second configuration of the artificial chordae, the second configuration of the artificial chordae being larger than the opening in the leaflet, a portion of the leaflet being disposed between the medial portion of the artificial chordae in the second configuration of the artificial chordae and the distal portion of the artificial chordae in the second configuration of the artificial chordae.

2. A method of repairing a prolapsed leaflet of a valve of a heart comprising:
    introducing into a ventricle of the heart a distal portion of a delivery system having a distal tip and carrying an artificial chordae having a distal portion and a proximal portion;
    disposing the distal tip of the delivery system in contact with a ventricular side of the leaflet;

while maintaining the entire distal portion of the delivery system on the ventricular side of the leaflet, extending from the distal tip of the delivery system a needle having a distal portion carrying the distal portion of the artificial chordae to pierce a prolapsed segment of the leaflet from the ventricular side of the leaflet to an atrial side of the leaflet to form an opening in the leaflet;

passing through the opening, from the ventricular side to the atrial side, the distal portion of the artificial chordae disposed in a first configuration, and with the proximal portion of the artificial chordae remaining on the ventricular side of the leaflet;

causing the distal portion of the artificial chordae to change from the first configuration to a second configuration, the second configuration being larger than the opening in the leaflet;

securing the artificial chordae to an apex region of the heart to reduce prolapse of the leaflet;

evaluating regurgitation of the valve while the heart is beating; and lengthening or shortening a distance between the leaflet and the apex region of the heart until regurgitation of the heart valve is reduced.

\* \* \* \* \*